US 6,904,324 B2

(12) United States Patent
Bishay

(10) Patent No.: US 6,904,324 B2
(45) Date of Patent: Jun. 7, 2005

(54) METHOD AND APPARATUS FOR DEPLOYING A PERCUTANEOUS PROBE

(75) Inventor: Jon M. Bishay, Woodinville, WA (US)

(73) Assignee: Meagan Medical, Inc., Reno, NV (US)

( * ) Notice: Subject to any disclaimer, the term of this patent is extended or adjusted under 35 U.S.C. 154(b) by 351 days.

(21) Appl. No.: 09/928,044

(22) Filed: Aug. 11, 2001

(65) Prior Publication Data

US 2003/0195599 A1 Oct. 16, 2003

Related U.S. Application Data

(63) Continuation-in-part of application No. 09/666,931, filed on Sep. 21, 2000, now Pat. No. 6,528,776, and a continuation-in-part of application No. 09/452,477, filed on Dec. 1, 1999, now Pat. No. 6,622,051.

(51) Int. Cl.[7] .................................................. A61N 1/05
(52) U.S. Cl. ........................ 607/149; 607/116; 606/129
(58) Field of Search ................................ 607/115, 116, 607/149; 600/372, 386–392; 606/129

(56) References Cited

U.S. PATENT DOCUMENTS

| 3,030,959 | A |   | 4/1962  | Grunert          |         |
|-----------|---|---|---------|------------------|---------|
| 3,090,151 | A |   | 5/1963  | Stewart et al.   |         |
| 3,208,452 | A |   | 9/1965  | Stern            |         |
| 3,938,526 | A |   | 2/1976  | Anderson et al.  |         |
| 3,943,935 | A |   | 3/1976  | Cameron          |         |
| 3,983,881 | A |   | 10/1976 | Wickham          |         |
| 4,139,011 | A |   | 2/1979  | Benoit et al.    |         |
| 4,153,059 | A |   | 5/1979  | Fravel et al.    |         |
| 4,207,903 | A |   | 6/1980  | O'Neill          |         |
| 4,256,116 | A |   | 3/1981  | Meretsky et al.  |         |
| 4,262,672 | A |   | 4/1981  | Kief             |         |
| 4,281,659 | A | * | 8/1981  | Farrar et al.    | 600/351 |
| 4,284,856 | A |   | 8/1981  | Hochmair et al.  |         |
| 4,381,012 | A |   | 4/1983  | Russek           |         |
| 4,408,617 | A |   | 11/1983 | Auguste          |         |

(Continued)

FOREIGN PATENT DOCUMENTS

| FR | 2500309       | 8/1982  |
|----|---------------|---------|
| FR | 2500745       | 9/1982  |
| GB | 2 163 355 A   | 2/1986  |
| GB | 2 255 719 A   | 11/1992 |
| WO | WO 01/39829 A1| 6/2001  |

OTHER PUBLICATIONS

U.S. Appl. No. 09/451,547, Bishay et al., filed Dec. 1, 1999.
U.S. Appl. No. 09/451,795, Leonard et al., filed Dec. 1, 1999.

(Continued)

*Primary Examiner*—George R. Evanisko
(74) *Attorney, Agent, or Firm*—Blank Rome LLP

(57) ABSTRACT

An apparatus for piercing a skin surface, and methods for operating and manufacturing such an apparatus. In one embodiment, the apparatus can include a support housing having an engaging surface to engage the skin surface. A releasable attachment member can releasably secure the housing to the skin surface, for example, with an adhesive bond. A stop member can operatively engage a percutaneous probe of the apparatus to at least restrict the ability of the probe to be re-used.

36 Claims, 10 Drawing Sheets

U.S. PATENT DOCUMENTS

| | | |
|---|---|---|
| 4,431,000 A | 2/1984 | Butler et al. |
| 4,437,467 A | 3/1984 | Helfer et al. |
| 4,512,351 A | 4/1985 | Pohndorf |
| 4,541,432 A | 9/1985 | Molina-Negro et al. |
| 4,556,064 A | 12/1985 | Pomeranz et al. |
| 4,583,549 A | 4/1986 | Manoli |
| 4,685,466 A | 8/1987 | Rau |
| 4,686,996 A | 8/1987 | Ulbrich |
| 4,712,558 A | 12/1987 | Kidd et al. |
| D297,047 S | 8/1988 | Hon et al. |
| 4,765,310 A | 8/1988 | Deagle et al. |
| 4,895,154 A | 1/1990 | Bartelt et al. |
| 4,934,371 A | 6/1990 | Malis et al. |
| 4,949,734 A | 8/1990 | Bernstein |
| 4,953,564 A | 9/1990 | Berthelsen |
| 4,979,508 A | 12/1990 | Beck |
| 5,012,811 A | 5/1991 | Malis et al. |
| D318,330 S | 7/1991 | Doty et al. |
| 5,036,850 A | 8/1991 | Owens |
| 5,054,486 A | 10/1991 | Yamada |
| 5,094,242 A | 3/1992 | Gleason et al. |
| 5,117,826 A | 6/1992 | Bartelt et al. |
| 5,211,175 A | 5/1993 | Gleason et al. |
| 5,246,014 A | 9/1993 | Williams et al. |
| 5,255,691 A | 10/1993 | Otten |
| 5,269,304 A | 12/1993 | Matthews |
| 5,281,218 A | 1/1994 | Imran |
| 5,332,401 A | 7/1994 | Davey et al. |
| D357,069 S | 4/1995 | Plahn et al. |
| 5,417,719 A | 5/1995 | Hull et al. |
| 5,423,314 A | 6/1995 | Schmid |
| 5,439,440 A | 8/1995 | Hofmann |
| 5,449,378 A | 9/1995 | Schouenborg |
| 5,593,429 A | 1/1997 | Ruff |
| 5,649,936 A | 7/1997 | Real |
| 5,682,233 A | 10/1997 | Brinda |
| 5,702,359 A | 12/1997 | Hofmann et al. |
| 5,810,762 A | 9/1998 | Hofmann |
| 5,851,223 A | 12/1998 | Liss et al. |
| 5,861,015 A | 1/1999 | Benja-Athon |
| 5,873,849 A | 2/1999 | Bernard |
| 5,928,144 A | 7/1999 | Real |
| 5,941,845 A | 8/1999 | Tu et al. |
| 5,948,008 A | 9/1999 | Daikuzono |
| 5,968,011 A | 10/1999 | Larsen et al. |
| 5,968,063 A | 10/1999 | Chu et al. |
| 6,009,347 A | 12/1999 | Hofmann |
| 6,032,064 A | 2/2000 | Devlin et al. |
| 6,035,236 A | 3/2000 | Jarding et al. |
| 6,050,992 A | 4/2000 | Nichols |
| 6,068,650 A | 5/2000 | Hofmann et al. |
| 6,117,077 A | 9/2000 | Del Mar et al. |
| 6,122,547 A | 9/2000 | Benja-Athon |
| 6,208,893 B1 | 3/2001 | Hofmann |
| 6,219,569 B1 | 4/2001 | Kelly et al. |
| D443,063 S | 5/2001 | Pisani et al. |
| 6,269,270 B1 | 7/2001 | Boveja |
| 6,304,785 B1 | 10/2001 | McCreery et al. |
| 6,341,237 B1 | 1/2002 | Hurtado |
| 6,355,021 B1 | 3/2002 | Nielsen et al. |
| 6,493,592 B1 | 12/2002 | Leonard et al. |
| 6,516,226 B1 | 2/2003 | Bishay et al. |
| 6,552,927 B2 | 2/2003 | Bishay et al. |
| 6,539,264 B1 | 3/2003 | Bishay et al. |
| 6,549,797 B1 | 4/2003 | Leonard et al. |
| 6,549,810 B1 | 4/2003 | Leonard et al. |
| 6,556,869 B1 | 4/2003 | Leonard et al. |
| 6,560,491 B1 | 5/2003 | Bishay et al. |

OTHER PUBLICATIONS

U.S. Appl. No. 09/451,796, Leonard et al., filed Dec. 1, 1999.
U.S. Appl. No. 09/451,799, Leonard et al., filed Dec. 1, 1999
U.S. Appl. No. 09/451,800, Bishay et al., filed Dec. 1, 1999.
U.S. Appl. No. 09/452,477, Bishay et al., filed Dec. 1, 1999.
U.S. Appl. No. 09/452,508, Leonard et al., filed Dec. 1, 1999.
U.S. Appl. No. 09/452,510, Bishay et al., filed Dec. 1, 1999.
U.S. Appl. No. 09/452,663, Bishay et al., filed Dec. 1, 1999.
U.S. Appl. No. 09/666,931, Leonard et al., filed Sep. 21, 2000.
U.S. Appl. No. 09/686,993, Gliner, filed Oct. 10, 2000.
U.S. Appl. No. 09/751,382, Bishay et al., filed Dec. 29, 2000.
U.S. Appl. No. 09/751,503, Gliner, filed Dec. 12, 2000.
U.S. Appl. No. 29/130,210, Leonard et al., filed Sep. 28, 2000.
U.S. Appl. No. 29/134,817, Bishay et al., filed Dec. 29, 2000.
*Starobinets, M. et al., "Analgesic Effect of High–Frequency and Acupuncture Like Transcutaneous Electric Stimulation of Nerve Fibers in Spinal Osteochondrosis," (Russian) Zhurnal Nevropatologii I Psikhiatrii Imeni S.S. Korsakova (1985) 85, (3) pp. 350–354.
Ulett, G. et al. "Electroacupuncture: Mechanisms and Clinical Application", Biological Psychiatry (Jul. 1998) 44: 129–38.
Van Doren, C.L., "Contours of Equal Perceived Amplitude and Equal Perceived Frequency for Electrocutaneous Stimuli," Perception and Psychophysics (1997) 59, (4), pp. 613–622.
White, P. et al. "Percutaneous Neuromodulation Therapy: Does the Location of Electrical Stimulation Effect the Acute Analgesic Response?", Anesthesia & Analgesia (Oct. 2000) 91:1–6.
White, P. et al. "The Effect of Montage on the Analgesic Response to Percutaneous Neuromodulation Therapy" Anesthesia & Analgesia (Feb. 2001) 92: 483–7.
PCT International Search Report for International Application No. PCT/US01/314441; mailed May 7, 2002; Applicant: Vertis Neuroscience, Inc., 8 pages.
PCT International Search Report for International Application No. PCT/US02/25551; mailed Feb. 18, 2003; Applicant: Vertis Neuroscience, Inc. 9 pgs.
Association for Advancement of Medical Instrumentation, "Implantable Peripheral Nerve Stimulators," American National Standard, ANSI/AAMI NS15–1995 pp. 1–8 NS15–1995 pp. 1–8.
Ahmed H. et al. "Percutaneous Electrical Nerve Stimulation (PENS): A Complementary Therapy for the Management of Pain Secondary to Bony Metastasis", The Clinical Journal of Pain (Dec. 1998) vol. 14, No. 4, pp. 320–3, Lippincott Williams & Wilkins, Philadelphia.
Ahmed H. et al. "Percutaneous Electrical Nerve Stimulation: An Alternative to Antiviral Drugs for Acute Herpes Zoster," Anesthesia & Analgesia (Oct. 1998) 87:911–4.
Almay, B.G.L. et al., "Long–Term High Frequency Transcutaneous Electrical Nerve Stimulation (hi–TNS) in Chronic Pain. Clinical Response and Effects on CSF Endorphins, Monoamine Metabolites, Substance P–Like Immunoreactivitiy (SPLI) and Pain Measures," Journal of Psycosomatic Research, (1985) vol. 29, No. 3, pp. 247–257, Pergamon Press Ltd. Great Britain.

Baker, L. L., et al. "Effects of Waveform on Comfort during Neuromuscular Electrical Stimulation," Clinical Orthopaedics and Related Research, Aug. 1998, No. 223, pp. 75–85.

Ballegaard, S. et al. "Acupuncture and Transcutaneous Electric Nerve Stimulation in the Treatment of Pain Associated with Chronic Pancreatitis. A Randomized Study", Scand. J. Gastroenterol. (Jun. 1985) 20: 1249–54.

Balogun, J. et al. "The effects of acupuncture, electroneedling and transcutaneous electrical stimulation therapies on peripheral haemodynamic functioning", Disability and Rehabilitation (Feb. 1998) vol. 20, No. 2, pp. 41–8, Taylor & Francis Ltd.

Balogun, J., "Effects of Ramp Time on Sensory, Motor and Tolerance Thresholds during Exogenous Electrical Stimulation," The Journal of Sports Medicine and Physical Fitness, (Dec. 1991) vol. 31, No. 4, pp. 521–526.

BD Microtainer Brand Safety Flow Lancet –Product Number 366356. BD catalog 1997–2000, http://catalog.bd.com/sctipts/OBDsheet.exe?FNC=productlist Alistproducts. html 3 66358 (Aug. 2001), 3 pages.

BD Safety Products. BD Vacutainer Safety–Lok Blood Collection Set; BD Vacutainer SafetyGlide Blood Collection Assembly and BD Vacutainer Eclipse Blood Collection Needle, 1 page.

BD Vacutainer SafetyGlide Blood Collection Assembly. Quick Reference Card (Oct. 1999), 1 page.

Brull, S. J., et al., "Pulse Width, Stimulus Intensity, Electrode Placement, and Polarity during Assessment of Neuromuscular Block," Anesthesiology, (Oct. 1995) V. 83, No. 4, pp. 702–709, Lippincott–Raven Publishers.

Bushnell M. C. et al. "Electrical stimulation of peripheral and central pathways for the relief of musculoskeletal pain", Can. J. Physiol. Pharmacol. (May 1991) 69:697703.

Carroll, D. et al., "Randomization is Important in Studies with Pain Outcomes; Systematic Review of Transcutaneous Electrical Nerve Stimulation in Acute Postoperative Pain," British Journal of Anesthesiology, (1996) vol. 77, pp. 798–803.

Cassuto, J. et al., "The Use of Modulated Energy Carried on a High Frequency Wave for the Relief of Intractable Pain," International Journal of Clinical Pharm. Research (1993) XI II (4) pp. 239–241.

Cheng R., Pomeranz, B. "Electroacupuncture analgesia could be mediated by at least two pain–relieving mechanisms: endorphin and non–endorphin systems", Life Sciences (Dec. 1979) 25: 1957–62, Pergamon Press Ltd.

Cheng R., et al. "Electroacupuncture elevates blood cortisol levels in naive horses; sham treatment has no effect", Intern. J. Neuroscience (Feb. 1980) vol. 10, pp. 95–7, Gordon and Breach Science Publishers, Inc., Great Britain.

Cheng R. S. S., Pomeranz, B. "Electrotherapy of Chronic Musculoskeletal Pain: Comparison of Electroacupuncture and Acupuncture–Like Transcutaneous Electrical Nerve Stimulation", The Clinical Journal of Pain (1987) vol. 2, No. 3, pp. 143–9, Raven Press, New York.

Cramp, A.F.L. et al., "The Effect of High–and Low–Frequency Transcutaneous Electrical Nerve STimulation Upon Cutaneous Blood Flow and Skin Temperature in Healthy Subjects," Clinical Physiology 20, (2000) 2, pp. 150–157, Blackwell Science Ltd.

Empi Eclipse+ Dual Channel Transcutaneous Electrical Nerve Stimulator User's Manual, Empi, Inc. (Sep. 1998), US Patent #D282,968, 31 pages.

Empi EPIX VT Dual Channel Transcutaneous Electrical Nerve Stimulator Instruction Manual, Empi, Inc. (1997) 22 pages.

Empi EPIX XL TENS Instruction Manual, Empi, Inc. (Sep. 1998) U.S. Patent No. D319,881, 22 pages.

Empi, Our Products: Electrotherapy for Rehabilitation, http://www.empi.com/b/b2.htm, (Mar. 2001), 3 pages.

Foster, N.E., et al., "Manipulation of Transcutaneous Electrical Nerve Stimulation Variables Has No Effect on Two Models of Experimental Pain in Humans," The Clinical Journal of Pain, (1996) 12; pp. 301–310, Lippincott–Raven Publishers, Philadelphia.

Gadsby, G. et al. "Nerve stimulation for low back pain –a review," Nursing Standard (Jul. 1997) vol. 11, No. 43, pp. 32–33.

Galleti, S.P., et al., "Highlights in the Subject of Low Frequency–High Intensity TENS," Minerva Stomatologica (Italy) (Sep. 1995), 44, pp. 421–429.

Ghoname, E. et al. "Does the Stimulus Frequency Affect the Analgesic Response to Electrical Stimulation?" Anesthesia & Analgesia (Nov. 1999) 88: S210, Lippincott Williams & Wilkins.

Ghoname, E. et al. "Percutaneous Electrical Nerve Stimulation for Low Back Pain", JAMA (Mar. 1999) vol. 281, No. 9, pp. 818–23.

Ghoname, E. et al. "Percutaneous electrical nerve stimulation: an alternative to TENS in the management of sciatica", Pain (Nov. 1999) 83: 193–9, Elsevier Science B.V.

Ghoname, E. et al. "The Effect of Stimulus Frequency on the Analgesic Response to Percutaneous Electrical Nerve Stimulation in Patients with Chronic Low Back Pain", Anesthesia & Analgesia (Oct. 1999) 88:841–6.

Ghoname, E. et al. "The Effect of the Duration of Electrical Stimulation on the Analgesic Response", Anesthesia & Analgesia (Jan. 1999) 88:S211.

Gopalkrishnan, P., et al., "Effect of Varying Frequency, Intensity, and Pulse Duration of Transcutaneous Electrical Nerve Stimulation on Primary Hyperalgesia in Inflamed Rats," Arch. Phys. Med. Rehabil., (Jul. 2000) vol. 81, pp. 984–990.

Gracanin, F., et al., "Optimal Stimulus Parameters for Minimum Pain in the Chronic Stimulation of Innervated Muscle," Arch. Phys. Med. Rehabil. (Jun. 1975) vol. 56, pp. 243–249.

Hamza, M. et al. "Effect of the Duration of Electrical Stimulation on the Analgesic Response in Patients with Low Back Pain", Anesthesiology (Dec. 1999), vol. 91, No. 6, pp. 1622–7, Lippincott Williams & Wilkins, Inc.

Hamza, M.A., et al., "Effect of the Frequency of Transcutaneous Electrical Nerve Stimulation on the Postoperative Opioid Angalgesic Requirement and Recovery Profile," Anesthesiology, (Nov. 1999) v. 91, No.5, pp. 1232–1238.

Han, J.S. et al., "Effect of Low–and High–Frequency TENS on Met–enkephalin–Arg Phe and dynorphin A immunoreactivity in human lumbar CSF," Pain (1991) vol. 47, pp. 295–298, Elsevier Science Publishers B.V.

Healthronics HANS LY257 User Manual, Healthronics Pte Ltd., Singapore, 15 pages.

Innovative Healthcare: Electrotherapy Pain & Rehabilitation Product Solutions from Rehabilicare.[Includes product description of SporTX and Ortho DX], http://www.mvp-design.com/sites/rehabilicare/all products. htmi, (Aug. 2001), 3 pages.

Intelect Legend Stim Clinical Reference Manual, vol. 4 Intelect Legend Series, Chattanooga Group, Inc., (Jul. 2000) 25 pages.

Jette, D. U. et al., "Effect of Different Forms of Transcutaneous Electrical Nerve Stimulation on Experimental Pain," Physical Therapy, (Feb. 1986) vol. 66/No. 2, pp. 187–193.

Johnson, M. I. et al., "Analgesic Effects of Different Pulse Patterns of Transcutaneous Electrical Nerve Stimulation on Cold–Induced Pain in Normal Subjects," Journal of Psychosomatic Research (1991) vol. 35, No.2/3, pp. 313–321, Great Britain.

Johnson, M. I. et al., "Analgesic Effects of Different Frequencies of Transcutaneous Electrical Nerve Stimulation on Cold–Induced Pain in Normal Subjects," Pain, (1989) 39, pp. 231–236, Elsevier Science Publishers B.V.

Johnson, M.I. et al., "An In–Depth Study of Long–Term Users of Transcutaneous Electrical Nerve Stimulation (TENS). Implications for Clinical Use of TENS," Pain (1991) 4, pp. 221–229, Elsevier Science Publishers B.V.

Katims, J.J. et al., "Transcutaneous Nerve Stimulation Frequency and Waveform Specificity in Humans," Appl. Neurophysiol. (1986) 49: pp. 86–91.

Landau, B. et al. "Neuromodulation Techniques for Medically Refractory Chronic Pain", Annu. Rev. Med. (Feb. 1993) 44: 279–87, Annual Reviews Inc.

Leem, J.W. et al., "Electrophysiological Evidence for the Antinociceptive Effect of Transcutaneous Electrical Stimulation on Mechanically Evoked Responsiveness of Dorsal Horns Neurons in Neuropathic Rats," Neuroscience Letters (1995) 192, pp. 197–200, Elsevier Science Ireland Ltd.

Lehmann T. et al. "Efficacy of Electroacupuncture and TENS in the Rehabilitation of Chronic Low Back Pain Patients", Pain (Sep. 1986) 26: 277–90, Elsevier Science Publishers B.V.

Liss, S. et al., "Physiological and Therapeutic Effects of High Frequency Electrical Pulses," Integrative Physiological and Behavioral Science, (Apr.–Jun. 1996) vol. 31, No. 2, pp . 88–94.

Marchand, S. et al., "Modulation of Heat Pain Perception by High Frequency Transcutaneous Electrical Nerve Stimulation (TENS)," The Clinical Journal of Pain (1991) 7: pp. 122–129, Raven Press Ltd., New York.

Model AWQ–104B Multi–Purpose Electronic Acupunctoscope Instruction Manual, 10 pages.

Moreno–Aranda, J. et al., "Electrical Parameters for Over–the–Skin Muscle Stimulation," J. Biomechanics, (1981) vol. 14, No. 9, pp. 579–585, Pergamon Press Ltd.

Moreno–Aranda, J. et al., "Investigation of Over–the–Skin Electrical Stimulation Parameters for Different Normal Muscles and Subjects," J. Biomechanics, (1981) vol. 14, No. 9, pp. 587–593, Pergamon Press Ltd., Great Britain.

O'Brien, W. J. et al., "Effect of Transcutaneous Electrical Nerve Stimulation on Human Blood B–Endorphin Levels," Physical Therapy, (Sep. 1984) vol. 64/ No. 9, pp. 1367–1374.

Omura, Y., "Basic Electrical Parameters for Safe and Effective Electro Therapeutics [Electro–Acupuncture, TES, TENMS, (or TEMS), TENS and Electro Magnetic Field Stimulation with or without Drug Field] for Pain, Neuromuscular Skeletal Problems, and Circulatory Disturbances," Acupuncture & Electro Therapeutics Res., Int. J. (1987) vol. 12, pp. 201–225, Pergamon Journals Ltd., USA.

Omura, Y., Electrical Parameters for Safe and Effective Electro–Acupuncture and Transcutaneous Electrical Stimulation: Threshold Potentials for Tingling, Muscle Contraction and Pain; and How to Prevent Adverse Effects of Electro–Therapy, Acupuncture and Electro–Therapeutics Res., Int. J., (1985) vol. 10, Pergamon Press Ltd. USA.

Ordog, G.J., "Transcutaneous Electrical Nerve Stimulation versus Oral Analgesic: A Randomized Double–Blind Controlled Study in Acute Traumatic Pain," American Journal of Emergency Medicine, (Jan. 1987) vol. 5, No. 1, , pp. 6–10.

Pointer F–3 Instruction Manual, ITO Co., Ltd., Tokyo, Japan (1999), 12 pages.

Radionics products brochure. "A Significant Breakthrough Using Pulsed Radiofrequency for Pain Management", includes RF Lesion Generator System, Model RFG–3C Plus, (1997), Radionics, Burlington, MA, 10 pages.

Rehabilicare Ortho Dx product brochure. "Reduce Rehabilitation Time and Enhance Patient Comfort with Ortho Dx", Rehabilicare, New Brighton, MN, 2 pages.

Rehabilicare SMP–plus product brochure. "SMP–plus. The Pain Relief Solution for Hard to Treat Patients", Rehabilicare, New Brighton, MN (1999) 2 pages.

Rehabilicare SporTX Product Data Sheet, 1 page.

Rehabilicare SporTX Quick Set–Up Instructions, "SPORTX. Get back in the GAME!", Rehabilicare, New Brighton, MN, 2 pages.

Romita, V.V. et al., "Parametric Studies on Electroacupuncture–Like Stimulation in a Rat Model; Effects of Intensity, Frequency, and Duration of Stimulation on Evoked Antinociception," Brain Research Bulletin, (1997) vol. 42, No. 4, pp. 289–296, Elsevier Science Inc., USA.

Rooney, J.G. et al., "Effect of Variation in the Burst and Carrier Frequency Modes of Neuromuscular Electrical Stimulation on Pain Perception of Healthy Subjects," Physical Therapy, (Nov. 1992) vol. 72, No. 11, pp. 800–809.

Sluka, K.A. et al., "Treatment with either High or Low Frequency TENS Reduces the Secondary Hyperalgesia Observed After Injection of Kaolin and Carrageenan into the Knee Joint," Pain, (1998) 77, pp. 97–102, Elsevier Science B.V.

Somers, D.L., et al., "High–Frequency Transcutaneous Electrical Nerve Stimulation Alters Thermal but not Mechanical Allodynia Following Chronic Constriction Injury of the Rat Sciatic Nerve," Arch. Phys. Med. Rehabil., (1998) 79, pp. 1370–1376.

* cited by examiner

METHOD AND APPARATUS FOR DEPLOYING A PERCUTANEOUS PROBE

CROSS-REFERENCE TO RELATED APPLICATIONS

The present application is a continuation-in-part of U.S. application Ser. No. 09/452,477, filed Dec. 1, 1999, now U.S. Pat. No. 6,622,051, and U.S. application Ser. No. 09/666,931, filed Sep. 21, 2000 now U.S. Pat. No. 6,528,776, both incorporated herein in their entireties by reference.

TECHNICAL FIELD

The present invention relates generally to methods and apparatuses for attaching, deploying, and detaching percutaneous probes, such as percutaneous electrodes used for electrical nerve stimulation.

BACKGROUND

Electrical therapy has long been used in medicine to treat pain and other conditions. For example, transcutaneous electrical nerve stimulation (TENS) systems deliver electrical energy through electrode patches placed on the surface of a patient's skin to treat pain in tissue beneath and around the location of the patches. One problem with TENS systems is that they may not provide patients with adequate pain relief.

More recently, a technique in which electrodes are placed through the patient's skin into the target tissue has been proposed. Percutaneous Neuromodulation Therapy ("PNT", also sometimes called Percutaneous Electrical Nerve Stimulation or "PENS") using percutaneously placed electrodes achieves significantly better pain relief results than TENS treatments using skin surface electrodes. This therapy is described in Ghoname et al., "Percutaneous Electrical Nerve Stimulation for Low Back Pain," *JAMA* 281:818–23 (1999); Ghoname et al., "The Effect of Stimulus Frequency on the Analgesic Response to Percutaneous Electrical Nerve Stimulation in Patients with Chronic Low Back Pain," *Anesth. Analg.* 88:841–6 (1999); Ahmed et al,. "Percutaneous Electrical Nerve Stimulation (PENS): A Complementary Therapy for the Management of Pain Secondary to Bony Metastasis," *Clinical Journal of Pain* 14:320–3 (1998); and Ahmed et al., "Percutaneous Electrical Nerve Stimulation: An Alternative to Antiviral Drugs for Herpes Zoster," *Anesth. Analg.* 87:911–4 (1998). The contents of these references are incorporated herein by reference.

One method for applying percutaneous nerve stimulation is to insert acupuncture needles into the patient's skin and attach the needles to waveform generators via cables and alligator clips to deliver a percutaneous electrical current. One drawback with this method is that the electrical connections to the needle may not be sufficiently secure and reliable. Another drawback with this method is that it may be difficult to accurately position the needles. Yet another drawback with acupuncture needles is that such needles may fail to provide adequate assurance to the practitioner and the patient that the needles have not been previously used. Accordingly, patients treated with such acupuncture needles may be at risk for exposure to pathogens transmitted by re-used needles.

SUMMARY

The present invention is directed to apparatuses and methods for attaching, detaching and deploying percutaneous probes. An apparatus in accordance with one aspect of the invention includes a housing supporting a percutaneous electrode in position to penetrate a skin surface of a recipient. The apparatus can further include a releasable attachment member having a first portion connected to the housing and a second portion with an attachment surface facing away from the housing to engage the recipient's skin surface. The second portion can be coupled to the first portion with a releasable bond, and a strength of the releasable bond can be less than the tear strength of the first portion and less than a tear strength of the second portion. For example, the releasable bond can include a plurality of connecting portions arranged along a line between the first and second portions, with the connecting portions separated by interstitial spaces.

In a further aspect of the invention, the support housing can include an engaging surface positioned to engage the skin surface of the recipient. The percutaneous electrode can be movable relative to the support housing in an axial direction toward and away from the engaging surface between a first position and a second position. The apparatus can further include a stop member coupled to the housing and movable relative to the housing between a non-restricting position and a restricting position. The stop member can be operatively decoupled from the percutaneous electrode when in the non-restricting position to allow axial motion of the electrode between the first and second positions. The stop member can be positioned to at least restrict motion of the percutaneous electrode away from the second position when the stop member is in the restricting position.

The invention is also directed toward a method for single-use application of a percutaneous electrode. In one aspect of the invention, the method can include positioning a housing proximate to a skin surface, coupling an attachment portion of the housing to the skin surface, deploying a percutaneous electrode by moving the electrode relative to the housing and through the skin surface of the recipient, and retracting the electrode from the skin surface and into the housing. The method can further include detaching the housing from the skin surface and at least substantially reducing an ability of the attachment portion to reattach to the same or different recipient.

The invention is also directed toward a method for re-using a percutaneous electrode configured for one-time use. The method can include positioning a housing proximate to a skin surface of a recipient, coupling an attachment portion of the housing to the skin surface of the recipient, deploying a percutaneous electrode by moving the electrode relative the housing and through the skin surface of the recipient, and retracting the electrode from the skin surface and into the housing. The method can further include detaching the housing from the skin surface and at least substantially reducing an ability of the attachment portion to reattach to the same or a different recipient, and then reattaching the attachment portion to a skin surface of the same or a different recipient. In another aspect of the invention, the method can include at least substantially reducing an ability of the percutaneous electrode to deploy in the skin surface of the same or a different recipient, and then redeploying the percutaneous electrode in the skin surface of the same or a different recipient.

Figure 1:
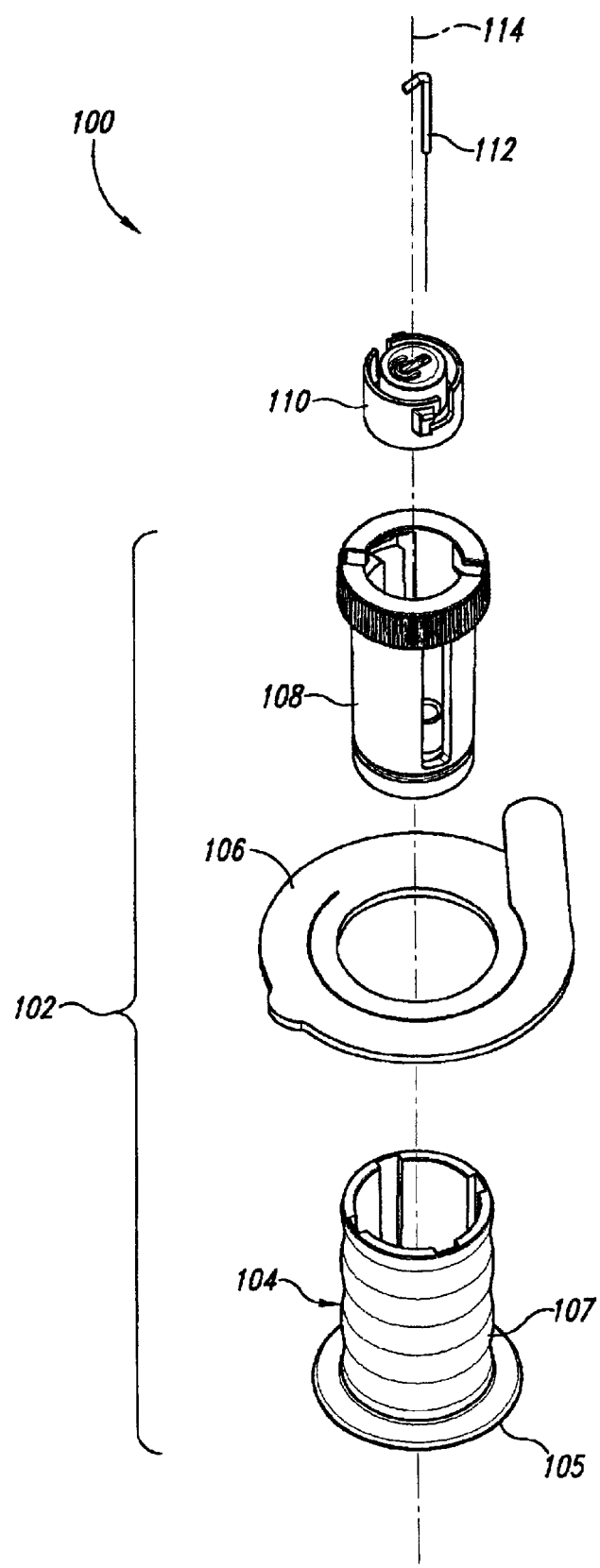
FIG. 1 is an exploded isometric view of a portion of a probe applicator in accordance with an embodiment of the invention.

In the drawings, identical references identify identical or substantially similar elements. To readily identify the discussion of any particular element, the most significant digit or digits in a reference number refer to the Figure number in which that element is first introduced (e.g., element 304 is first introduced and discussed in FIG. 3 and element 1002 is first introduced and discussed in FIG. 10).

DETAILED DESCRIPTION

Many specific details of certain embodiments of the invention are set forth in the following description and in FIGS. 1–15B to provide a thorough understanding of these embodiments. One skilled in the art, however, will understand that the present invention may have additional embodiments, or that the invention may be practiced without several of the details described below. Additionally, the following pending U.S. patent application Ser. Nos. are incorporated herein in their entirety by reference: 09/452,663; 09/452,508; 09/451,795; 09/451,799; 09/452,510; 09/451,800; 09/451,796; 09/451,547; 09/667,183 (attorney docket number 33734.8002US00); and 29/130,210 (attorney docket number 33734.8001.US01).

The present invention describes methods and apparatuses for attaching, deploying, and detaching probes, such as electrical therapy electrodes that deliver electrical current to a region of a patient's tissue by piercing the skin covering the tissue. The electrical current is generated by a control unit external to the patient and typically has particular waveform characteristics, such as frequency, amplitude and pulse width. Depending on the treatment or therapy being delivered, there may be one electrode containing both a cathode and an anode or a plurality of electrodes with at least one serving as a cathode and at least one serving as an anode.

FIGS. 1–6 and the associated discussion refer generally to an applicator in accordance with an embodiment of the invention. FIGS. 7–13 and the associated discussion refer generally to methods and devices for attaching and detaching an applicator in accordance with embodiments of the invention. FIGS. 14A–15B and the associated discussion refer generally to methods and apparatuses for preventing reinsertion of previously inserted percutaneous probes.

FIG. 1 is an exploded top isometric view of probe applicator 100 that includes a housing 102 in accordance with an embodiment of the invention. The housing 102 can include a base 104 that rests on the patient's skin, an attachment member 106 (such as an adhesive pad) to attach the base 104 to the skin, and a sleeve 108 received in the base 104. The base 104 can include a skin engaging surface and a casing. For example, the skin engaging surface can be an annular lip 105 and the casing can be a tube 107 projecting from the lip 105 at a desired angle. A slider 110 fits in the sleeve 108 and supports a probe 112 for movement relative to the base 104. The probe 112 can include an electrode, a diagnostic probe, a drug delivery needle, a liquid extraction needle, or another transcutaneous or percutaneous device.

In operation, the slider 110 can slide downwardly and upwardly within the sleeve 108 to insert and retract the probe 112. The slider 110 and the sleeve 108 can rotate as a unit to selected positions relative to the base 104. In one aspect of this embodiment, the slider 110, the sleeve 108, and the base 104 are all coaxial with a central axis 114 of the housing 102, and the probe 112 is offset or eccentric relative to the central axis 114. Accordingly, when the slider 110 and the sleeve 108 are rotated together as a unit relative to the base 104, the probe 112 orbits about the central axis 114 to a new position relative to the patient's skin surface. In an alternate embodiment, the slider 110 and the sleeve 108 need not rotate relative to the housing 102, and the probe 112 can move axially along the central axis 114. In a further alternate embodiment, the sleeve 108 can be eliminated and the housing 102 alone can guide the slider 110.

Figure 2:
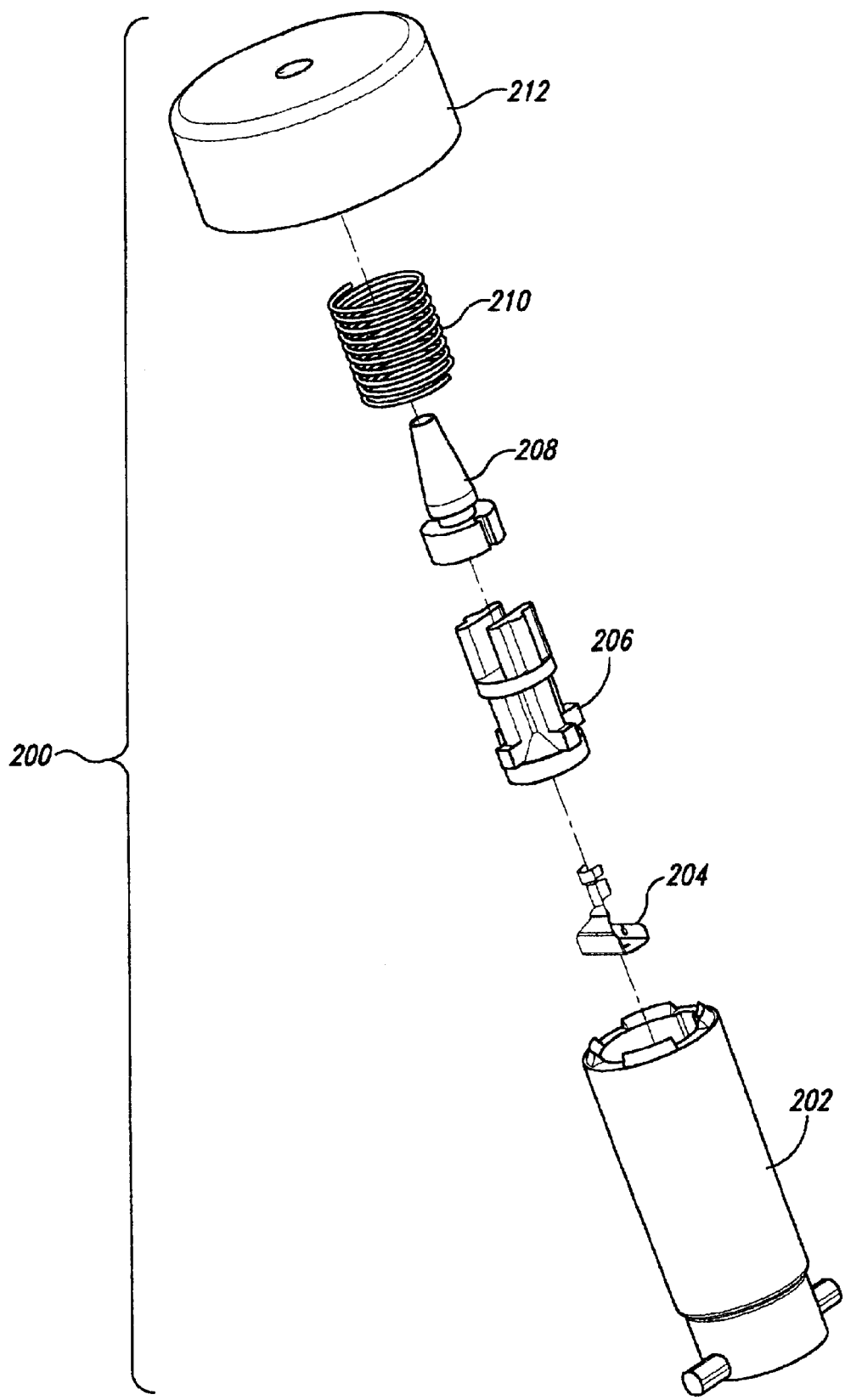
FIG. 2 is an exploded isometric view of an actuator that operates with the applicator shown in FIG. 1 in accordance with an embodiment of the invention.

FIG. 2 is an exploded top isometric view of an actuator 200 that engages the slider 110 (FIG. 1) and moves the slider 110 and the probe 112 (FIG. 1) in accordance with an embodiment of the invention. In one aspect of this embodiment, the actuator 200 can include a plunger 202 that releasably engages the slider 110 and translates the slider 110 axially within the sleeve 108 (FIG. 1). The actuator 200 can further include a contact plate 204 supported by a contact support 206 and biased against the probe 112 by a spring 210. A wire (not shown in FIG. 2) is connected to the contact 204 and passes through a grommet 208 and a cap 212 for coupling the contact 204 to a source of electrical power.

Figure 3:
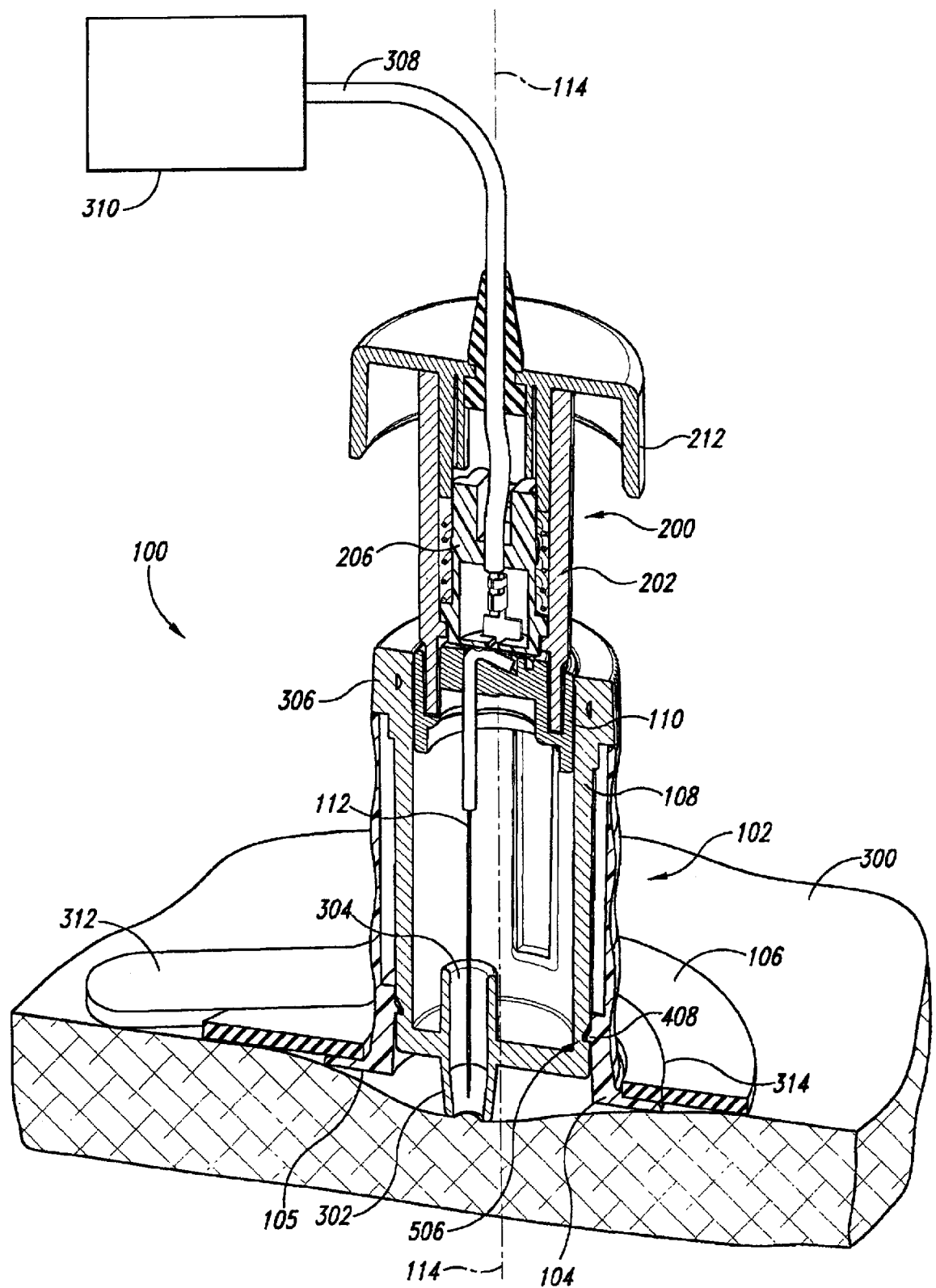
FIG. 3 is a partially schematic, cut-away side elevational view of the actuator shown in FIG. 2 coupled to the applicator shown in FIG. 1 and a power source in accordance with an embodiment of the invention.

FIG. 3 is a cut-away side isometric view of the apparatus 100 described above with reference to FIGS. 1 and 2 positioned on the surface of a patient's or recipient's skin 300 in accordance with an embodiment of the invention. In one aspect of this embodiment, the base 104 has a flat lower surface and is releasably attached to the skin 300 with the attachment member 106. The base 104 is accordingly stably mounted to the skin 300, and the lip 105 of the base 104 is configured to direct the probe 112 at a right angle into the skin 300. The lip 105 of the base 104 can alternatively be configured to direct the probe 112 at another angle into the skin 300 in accordance with another embodiment of the invention. A probe tube 302 protrudes downwardly beneath the base 104 and includes a tube channel 304 through which the probe 112 passes. Accordingly, the probe tube 302 depresses and stretches the skin 300 beneath the base 104, while allowing the skin 300 to bulge upwardly slightly within the tube channel 304. As a result, the patient may be less aware of and/or less alarmed by the passage of the probe 112 into the skin 300.

The probe 112 is inserted into the skin 300 by grasping the cap 212 of the actuator 200 and depressing the plunger 202 until the slider 110 contacts the top of the probe tube 302. If the probe 112 is to be repositioned in the skin 300, the plunger 202 is raised until the slider 110 is aligned with a sleeve rim 306 of the sleeve 108, as shown in FIG. 3. The practitioner then grasps the sleeve rim 306 and rotates the sleeve 108, the slider 110 and the plunger 202 about the central axis 114 within the base 104 to a new position relative to the skin surface 300. As the slider 110 rotates about the axis 114, the eccentric probe 112 and the probe tube 302 orbit about the axis 114 to the new position. Once the sleeve 108 is in the new position, the practitioner depresses the plunger 202 to reinsert the probe 112 in the new position.

When the probe 112 includes an electrode for percutaneous electrical nerve stimulation, the practitioner then couples an electrical lead 308 between the probe 112 and a control unit 310 that supplies electrical power to the probe 112. In one embodiment, the control unit 310 supplies a current-regulated and current-balanced waveform with an amplitude of up to 20 milliamps, a frequency of from approximately 4 Hz to approximately 5 Hz, and a pulse width of from approximately 50 microseconds to approximately 1 millisecond. In other embodiments, the control unit 310 can supply other waveforms having other characteristics. In still further embodiments, the control unit 310 can control the voltage applied to the probe 112 in addition to or in lieu of controlling the current.

In one embodiment, the housing 102 remains in place on the patient's skin 300 throughout the treatment, which can last 30 minutes in one aspect of this embodiment. When the treatment is complete, the housing 102 may be removed by first retracting the probe 112 from the skin 300, following the steps described above in reverse order. The housing 102 can then be lifted from the skin 300 after releasing the attachment member 106 from the skin 300. In one aspect of this embodiment, the attachment member 106 can include a non-adhesive tab portion 312 and a perforated slit 314 to facilitate removing the attachment member 106. A new housing 102 can be attached to the patient for each subsequent treatment. Alternatively, the housing 102 can remain attached to the patient for more than one treatment session.

Figure 4:
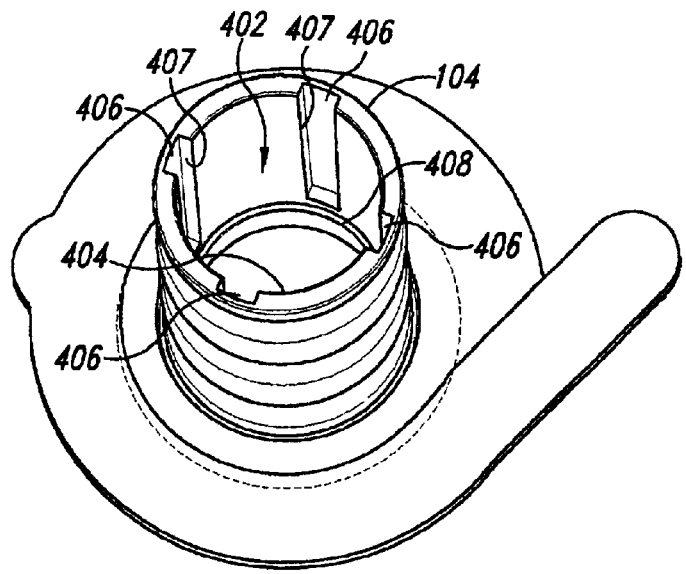
FIG. 4 is a top isometric view of a base of an applicator in accordance with an embodiment of the invention.
Figure 5:
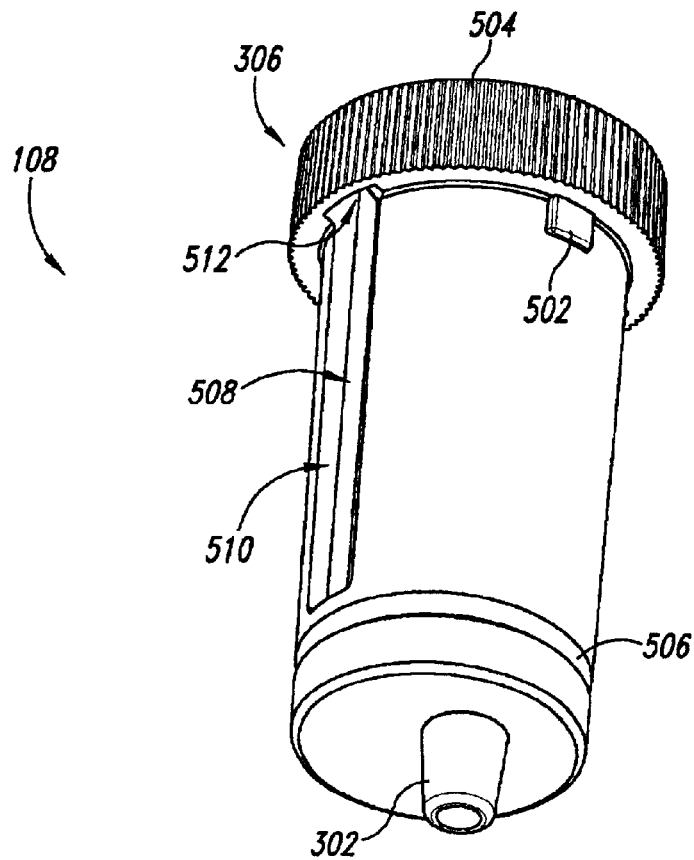
FIG. 5 is a bottom isometric view of an applicator sleeve in accordance with an embodiment of the invention.

FIG. 4 is a top isometric view of an embodiment of the base 104 shown in FIGS. 1 and 3. FIG. 5 is a bottom isometric view of an embodiment of the sleeve 108 shown in FIGS. 2 and 3. Referring now to FIGS. 4 and 5, the base 104 can include a hollow receiving cylinder 402 sized to rotatably receive the sleeve 108. The receiving cylinder 402 can have an inner surface 404 with a plurality of axial base channels 406 defined by channel walls 407 and sized to receive corresponding sleeve locator tabs 502 of the sleeve 108. In one aspect of this embodiment, the sleeve 108 can include two oppositely facing sleeve locator tabs 502 (one of which is visible in FIG. 5) and the base 104 can include two pairs of oppositely facing axial channels 406. In other embodiments, the sleeve 108 can have a different number of sleeve locator tabs 502, and/or the base 104 can have a different number of axial base channels 406. In either embodiment, the practitioner can rotate the sleeve 108 relative to the base 104 by grasping finger grips 504 disposed around the sleeve rim 306 and twisting the sleeve 108 clockwise or counterclockwise to force the sleeve locator tabs 502 out of one pair of axial base channels 406 and into the next pair of axial base channels 406.

In one aspect of an embodiment shown in FIGS. 4 and 5, the practitioner is at least restricted from (or prevented from) moving the sleeve 108 axially relative to the base 104 by a retaining lip 408 in the base 104 that projects radially inwardly from the inner surface 404 and is received in a corresponding retaining groove 506 in the sleeve 108. The retaining lip 408 can have a downwardly tapered side surface that snaps into the retaining groove 506 when the sleeve 108 is initially inserted into the base 104 during installation. The retaining lip 408 can also have a downwardly facing step surface that engages a corresponding upwardly facing surface of the retaining groove 506 to prevent further axial movement of the sleeve 108 relative to the base 104, while allowing rotational movement of the sleeve 108 relative to the base 104 (as is also shown in FIG. 3).

In one embodiment, the sleeve 108 has two sleeve axial guide channels 508 that align with a corresponding pair of the axial base channels 406 in the base 104 when the sleeve tabs 502 are positioned in the other pair of axial base channels 406. Each sleeve axial guide channel 508 includes a lower portion 510 that is coextensive with one of the axial base channels 406 and an upper portion 512 in the rim 306 above the axial base channels 406. This arrangement can prevent the practitioner from simultaneously moving the probe 112 (FIG. 3) axially and transversely relative to the patient's skin 300 (FIG. 3). As described below with reference to FIG. 6, this arrangement can also prevent the practitioner from moving the probe 112 transversely relative to the skin 300 until the probe 112 is fully retracted from the skin 300.

Figure 6:
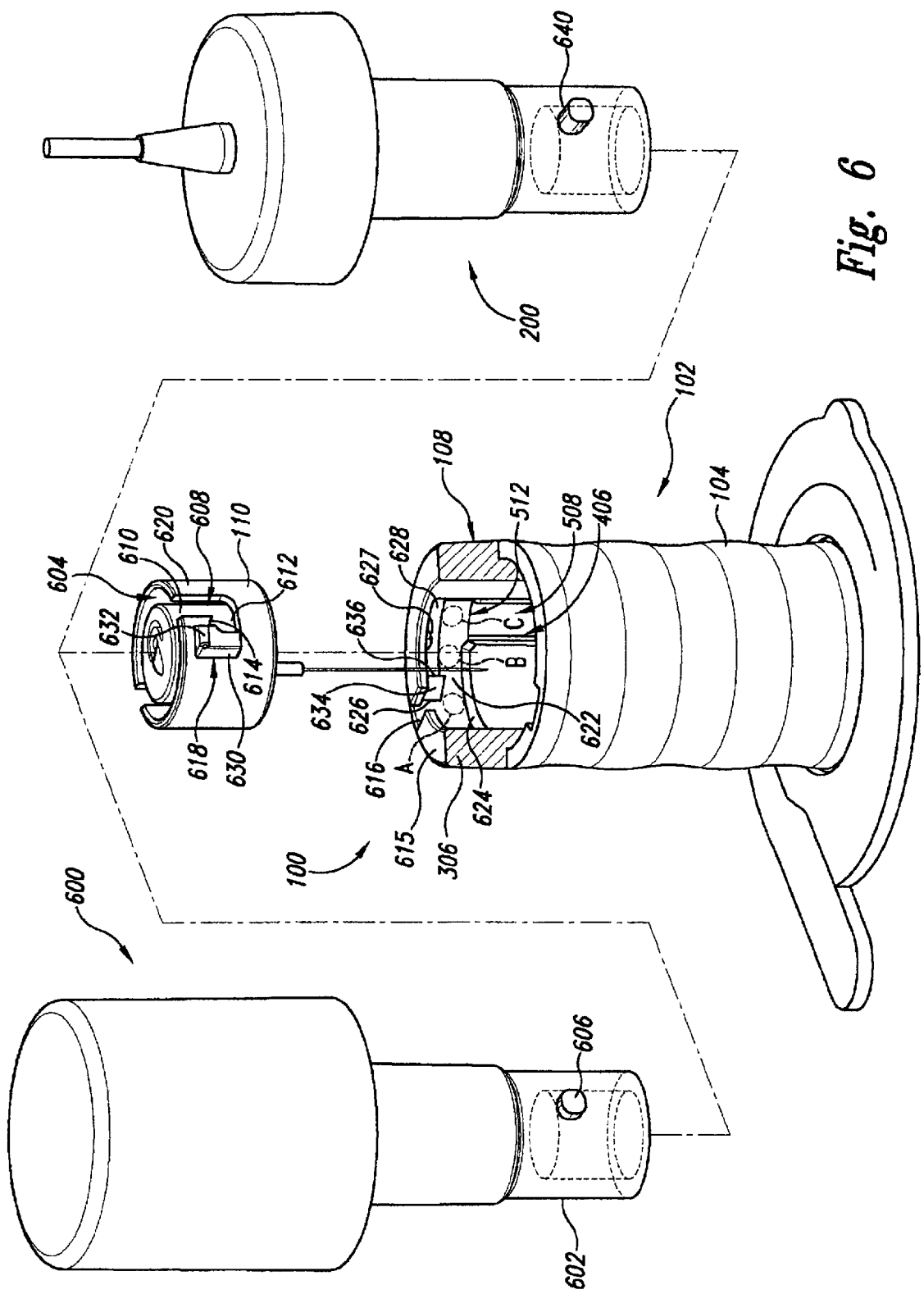
FIG. 6 is an exploded side isometric view of a slider, an assembly tool, and an actuator positioned adjacent to an applicator base in accordance with an embodiment of the invention.

FIG. 6 is a top isometric view of the slider 110 positioned above the sleeve 108, which has been inserted into the base 104 of the applicator 100 in accordance with an embodiment of the invention. In one aspect of this embodiment, the slider 110 is installed in the housing 102 during assembly by operating an assembly tool 600. Once installed, the slider 110 can be moved relative to the housing 102 by the practitioner, who can engage the slider 110 with the actuator 200. The operations of the assembly tool 600 and the actuator 200 are described in turn below.

In one embodiment, the assembly tool 600 includes a thin-walled cylinder 602 that is removably received in a corresponding circular groove 604 in the slider 110. The assembly tool 600 can also include two assembly pegs 606

(one of which is visible in FIG. 6) that are received in corresponding peg channels 608 of the slider 110. Each peg channel 608 can include an axial portion 610 and a transverse portion 612. The transverse portion 612 can have a curved upper surface 614 shaped to receive the assembly peg 606. To engage the assembly tool 600 with the slider 110, the installer aligns the assembly pegs 606 of the assembly tool 600 with the axial portions 610 of the peg channels 608. The installer then lowers the assembly tool 600 into the circular groove 604 of the slider 110. When the assembly pegs 606 reach the bottom of the axial portions 610 of the peg channels 608, the installer rotates the assembly tool 600 clockwise until the assembly pegs 606 reach the clockwise ends of the transverse portions 612 of the peg channels 608. The installer can then release downward pressure on the assembly tool 600 to allow the spring 210 (FIG. 3) to bias the assembly pegs 606 upwardly against the upper surface 614 of the peg channels 608 and retain the slider 110 in engagement with the tool 600. In one aspect of this embodiment, each assembly peg 606 is flush with or recessed from an outer surface 620 of the slider 110 so as not to interfere with the motion of the slider 110 into the sleeve 108, as described below.

In one embodiment, the slider 110 includes two guide members 618 (one of which is visible in FIG. 6). The rim 306 of the sleeve 108 has a flat, transverse lip 615 with oppositely facing apertures 616 (one of which is visible in FIG. 6), each sized to receive one of the guide members 618. In one aspect of this embodiment, one guide member 618 can be larger than the other, and one aperture 616 can be larger than the other so that the slider 110 can be inserted into the sleeve 108 in only one orientation. Accordingly, the probe 112 will automatically align with the probe tube 302 (FIG. 3). Alternatively, both guide members 618 can have approximately the same size. In either embodiment, the assembly tool 600 and the slider 110 are both lowered as a unit toward the housing 102 until the guide members 618 are received in the apertures 616 of the rim 306.

The rim 306 of the sleeve 108 can have transverse guide channels 622 that extend between each of the apertures 616 and a corresponding upper portion 512 of one of the sleeve axial guide channels 508. Each transverse guide channel 622 is defined in part by a channel floor 624 and includes a rotational stop 626 to restrict counterclockwise rotation of the slider 110. The transverse guide channel 622 can further include a sleeve rotational restriction 627 that extends axially downwardly from the lip 306 into the transverse guide channel 622 to restrict rotational motion of the slider 110. A sleeve axial restriction 628 is offset axially downwardly from the rim 615 and can extend radially inwardly to engage the guide members 618 and restrict axial motion of the slider 110. Accordingly, the sleeve rotational restriction 627 cooperates with a slider rotational restriction 630 of the slider 110, and the sleeve axial restriction 628 cooperates with a slider axial restriction 632 of the slider 110, as described in greater detail below.

When the slider 110 and the assembly tool 600 are lowered into the apertures 616, the assembly pegs 606 are received in the transverse guide channels 622 of the sleeve rim 306, with one of the assembly pegs 606 at position "A" (indicated by dashed lines in FIG. 6). The guide members 618 are also positioned in the transverse guide channel 622 adjacent to the assembly pegs 606. When the installer rotates the assembly tool 600 clockwise, the slider rotational restriction 630 passes over an inclined ramp surface 634 of the rotational stop 626 and then snaps into place against the sleeve rotational restriction 628. The assembly pegs 606 are now at position "B," and the axial portions 610 of the peg channels 608 in the slider 110 are aligned with the apertures 616. Because a rear surface 636 of the rotational stop 626 is flat and directly faces the slider rotational restriction 630, the slider 110 is prevented from rotating counterclockwise past the rotational stop 626. At this point, the slider rotational restriction 630 engages the sleeve rotational restriction 626 and the slider axial restriction 632 rides along the upper surface of the sleeve axial restriction 628 just beneath the rim 615. The slider 110 is now installed in the housing 102 and the assembly tool 600 is removed by depressing the tool 600 slightly to disengage the assembly pegs 606 from the upper surfaces 614 of the peg channels 608. The installer then rotates the assembly tool 600 counterclockwise until the assembly pegs 606 are aligned with the axial portions 610 of the peg channels 608 at position "A", and lifts the assembly tool 600 clear of the slider 110 and the housing 102. In one aspect of this embodiment, the housing 102 with the slider 110 installed can now be provided to an end user or practitioner along with a separate actuator 200.

To operate the probe applicator 100, the practitioner attaches the applicator 100 to the patient's skin 300, as described above with reference to FIG. 3. The practitioner then engages the actuator 200 shown in FIG. 6 with the slider 110 by aligning actuator pegs 640 with the apertures 616 in the rim 306 of the housing 102, and lowering the actuator pegs 640 into the apertures 616. The practitioner rotates the actuator 200 until the actuator pegs 640 engage the slider 110. At this point, one of the actuator pegs 640 is located at position "B" in the transverse guide channel 622. The practitioner then continues to rotate the actuator 200 clockwise, forcing each guide member 618 past the corresponding sleeve rotational restriction 627 until the one actuator peg 640 is at position "C." At this point, the guide members 618 and the actuator pegs 640 are aligned with the upper portion 512 of the sleeve axial guide channel 508 and the base axial channel 406. When the slider rotational restriction 630 of guide member 618 "clicks" past the sleeve rotational restriction 627, the practitioner receives mechanical and/or audio feedback indicating that the slider 110 has the proper rotational position for inserting the probe 112 into the patient.

To insert the probe 112 into the patient, the practitioner exerts a downward force on the actuator 200, forcing the slider axial restrictions 632 over the sleeve axial restrictions 628 until the slider axial restriction 632 "clicks" over the sleeve axial restriction 628, giving the practitioner additional mechanical feedback indicating that the slider 110 is correctly positioned for continued insertion. The practitioner then depresses the actuator 200, forcing the slider 110 downwardly through the sleeve 108 with less mechanical resistance than was required to snap the slider axial restrictions 632 over the sleeve axial restrictions 628. The downward movement of the slider 110 through the sleeve 108 moves the probe 112 downwardly through the probe tube 302. In one aspect of this embodiment, the weight of the slider 110 is sufficient to cause it to descend freely downwardly, and the only force exerted by the practitioner is the force necessary to insert the probe 112 into the patient. As the slider 110 moves downwardly, the sleeve axial guide channels 508 guide the guide members 618 along an axial path, and the base axial channels 406 receive and guide the actuator pegs 640 along a parallel axial path.

If the probe 112 is to be repositioned, the practitioner moves the actuator 200 and the slider 110 upwardly, with the sleeve axial guide channels 508 guiding the guide members 618 and the base axial channels 406 guiding the actuator pegs 640 to ensure that the motion of the probe 112 is moved only in the axial direction. If the practitioner attempts to rotate the rim 306 before the slider 110 has been fully retracted so that the slider axial restrictions 632 snap into position above the sleeve axial restrictions 628, the actuator pegs 640 will bear against the channel walls 407 (FIG. 4) of the base axial channel 406, preventing such rotation. The practitioner continues to raise the actuator 200 and the slider 110 until the slider axial restrictions 632 snap back over the sleeve axial restrictions 628 to ensure that the one actuator peg 640 is located in the transverse guide channel 622 at position "C." At this point, the probe 112 has been completely retracted from the skin 300 (FIG. 3) and the sleeve axial restrictions 628 can keep the slider 110 and the probe 112 from sliding downwardly until the practitioner is ready to re-insert the probe 112. The practitioner then rotates the slider 110, the probe 112, the actuator 200 and the sleeve 108 as a unit by grasping the rim 306 of the sleeve 108 and rotating the rim 306 relative to the base 104, as described above with reference to FIG. 3. Once the probe 112 has been rotated to the new position, the practitioner re-inserts the probe 112. Accordingly, the sleeve axial channels 508, the base axial channels 406, and the transverse channels 622 of the rim 306 sequentially guide the probe 112 axially and transversely relative to the skin 300.

One feature of an embodiment of the probe applicator 100 described above with reference to FIGS. 1–6 is that the arrangement of the housing 102, the slider 110 and the actuator 200 allows the practitioner to re-position the probe 112 transversely relative to the patient's skin (by orbiting the probe 112 about the central axis 114), and allows the practitioner from moving the probe 112 axially (for probe insertion and retraction), but prevents the practitioner from moving the probe 112 transversely until the probe 112 is completely removed from the patient. An advantage of this feature is that the practitioner will be less likely to harm the patient by moving the probe 112 transversely while the probe 112 is still inserted in the patient.

Another advantage of an embodiment of the applicator 100 described above with reference to FIGS. 1–6 is that the practitioner can reposition the probe 112 relative to the patient's skin 300 without disengaging the entire housing 102 from the patient. For example, when the probe 112 is an electrical stimulation needle, the practitioner can fasten the housing 102 to the skin 300 above the general location of the nerve region that is to receive electrical stimulation and then fine-tune the location by rotating the probe 112 relative to the housing 102 while the housing 102 remains attached to the patient's skin 300. In one embodiment, the probe 112 can be offset from the central axis 114 by a distance of 0.090 inches, and can be positioned in one of four preselected positions, with each preselected position being approximately 0.127 inches from an adjacent position. In other embodiments, the probe 112 can be moved to more or fewer preselected positions, and the preselected positions can be separated by greater or lesser distances.

Figure 7:
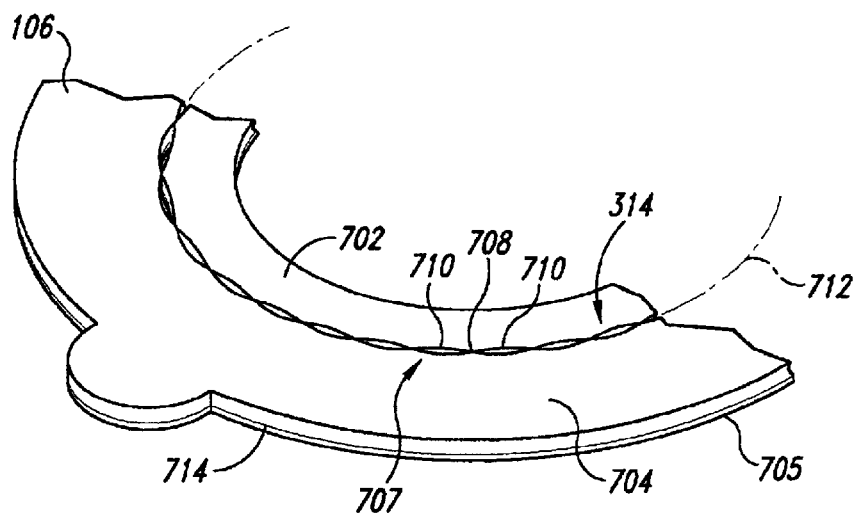
FIG. 7 is an isometric view of a portion of an attachment member for a probe applicator in accordance with an embodiment of the invention.

FIG. 7 is an isometric view of a portion of an attachment member 106 generally similar to that described above with reference to FIGS. 1 and 3 in accordance with an embodiment of the invention. In one aspect of this embodiment, the attachment member 106 can include a compressible foam body having a first portion 702 connected to a second portion 704 with a releasable bond 707. The releasable bond 707 can be aligned with a tear line 712 that allows the practitioner to tear at least a part of the second portion 704 away from the first portion 702 after the application 100 (FIG. 1) has been used.

In one aspect of this embodiment, the attachment member 106 can include a downwardly facing adhesive surface 714 that extends over both the first portion 702 and the second portion 704. For example, the attachment member 106 can include a polyethylene foam with an acrylic sheet adhesive, available from Scapa Medical of Inglewood, Calif. Accordingly, the first portion 702 can be adhesively bonded to the annular lip 105 (FIG. 1) of the housing 102 (FIG. 1) by engaging the downwardly facing adhesive surface 714 of the first portion 702 with an upwardly facing surface of the lip 105. In other embodiments, the first portion 702 can be attached to the lip 105 with other devices. In any of the foregoing embodiments, the adhesive surface 714 of the second portion 704 can be adhesively bonded to the patient's skin. In one aspect of this embodiment, a cover 705 (such as a coated paper sheet) can be initially adhered to the adhesive surface 714 of the second portion 704, and can be removed prior to engaging the adhesive surface 714 with the patient's skin.

In one embodiment, the releasable bond 707 can include a perforated slit 314 having connecting portions 708 that connect the first portion 702 to the second portion 704, with interstitial spaces 710 between the connecting portions 708. For example, the first portion 702 can be formed integrally with the second portion 704, and the interstitial spaces 710 can be formed by piercing the attachment member 106 at spaced-apart locations along the tear line 712. Alternatively, the first portion 702 can be initially separate from the second portion 704 and can be connected with connecting portions 708 formed, for example, by drops of liquid cement. In other embodiments, the construction of the releasable bond 707 can have other arrangements, such as those described below with reference to FIGS. 8A–8C. In any of these embodiments, the attachment member 106 will tend to preferentially separate at the releasable bond 707 and along the tear line 712 because the tear strength of the releasable bond 707 is less than the tear strength of both the first portion 702 and the second portion 704.

Figure 8A:
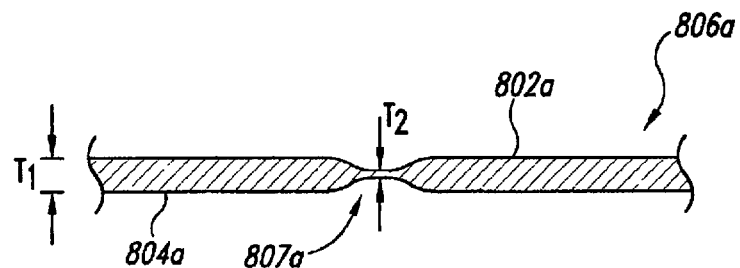
FIG. 8A is a cross-sectional side elevational view of a portion of an attachment member in accordance with another embodiment of the invention.

FIG. 8A is a cross-sectional side elevational view of a portion of an attachment member 806a in accordance with another embodiment of the invention. In one aspect of this embodiment, the attachment member 806a can include a first portion 802a and a second portion 804a generally similar in shape to the first portion 702 and the second portion 704, respectively, described above with reference to FIG. 7. The attachment member 806a can further include a releasable bond 807a between the first portion 802a and the second portion 804a. In one aspect of this embodiment, the first and second portions 802a, 804a can have a material thickness $T_1$ that is greater than a thickness $T_2$ of the releasable bond 807a. Accordingly, when opposing forces are applied to the first portion 802a and the second portion 804a, the attachment member 806a will tend to separate at the releasable bond 807a.

Figure 8B:
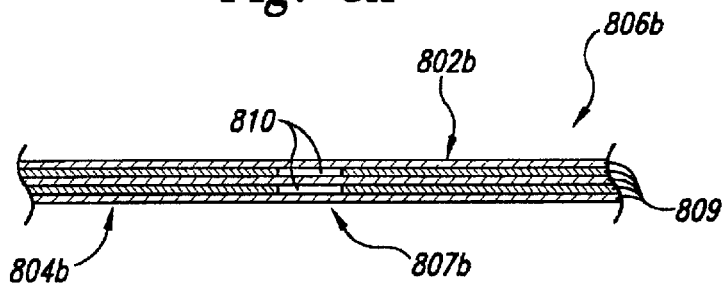
FIG. 8B is a cross-sectional side elevational view of a portion of an attachment member in accordance with still another embodiment of the invention.

FIG. 8B is a cross-sectional side elevational view of a portion of an attachment member 806b in accordance with yet another embodiment of the invention. In one aspect of this embodiment, the attachment member 806b can include a first portion 802b and a second portion 804b connected with a releasable bond 807b. The first and second portions 802b and 804b can each include a plurality of stacked layers 809. In the region of the releasable bond 807b, one or more of the layers 809 can be eliminated, leaving gaps 810 between adjacent layers 809. Accordingly, the releasable bond 807b will be weaker than both the first portion 802b and the second portion 804b, and will tend to tear when the practitioner applies opposing forces to the first and second portions 802b, 804b.

Figure 8C:
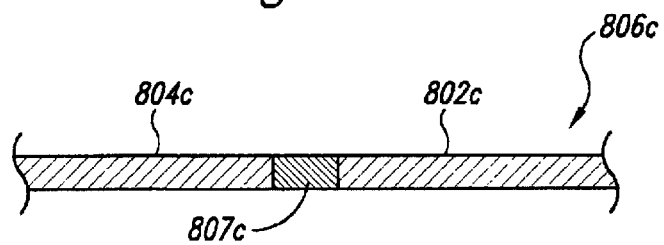
FIG. 8C is a cross-sectional side elevational view of a portion of an attachment member in accordance with yet another embodiment of the invention.

FIG. 8C is a cross-sectional side elevational view of a portion of an attachment member 806c having a first portion 802c coupled to a second portion 804c with a releasable bond 807c in accordance with another embodiment of the invention. In one aspect of this embodiment, the material forming the releasable bond 807c can have about the same thickness as the material forming both the first portion 802c and the second portion 804c, but can have a lower tear strength than either the first portion 802c or the second portion 804c. Accordingly, at least part of the second portion 804c will tend to separate from the first portion 802c at the releasable bond 807c when opposing forces are applied to the first and second portions 802c, 804c.

Figure 9:
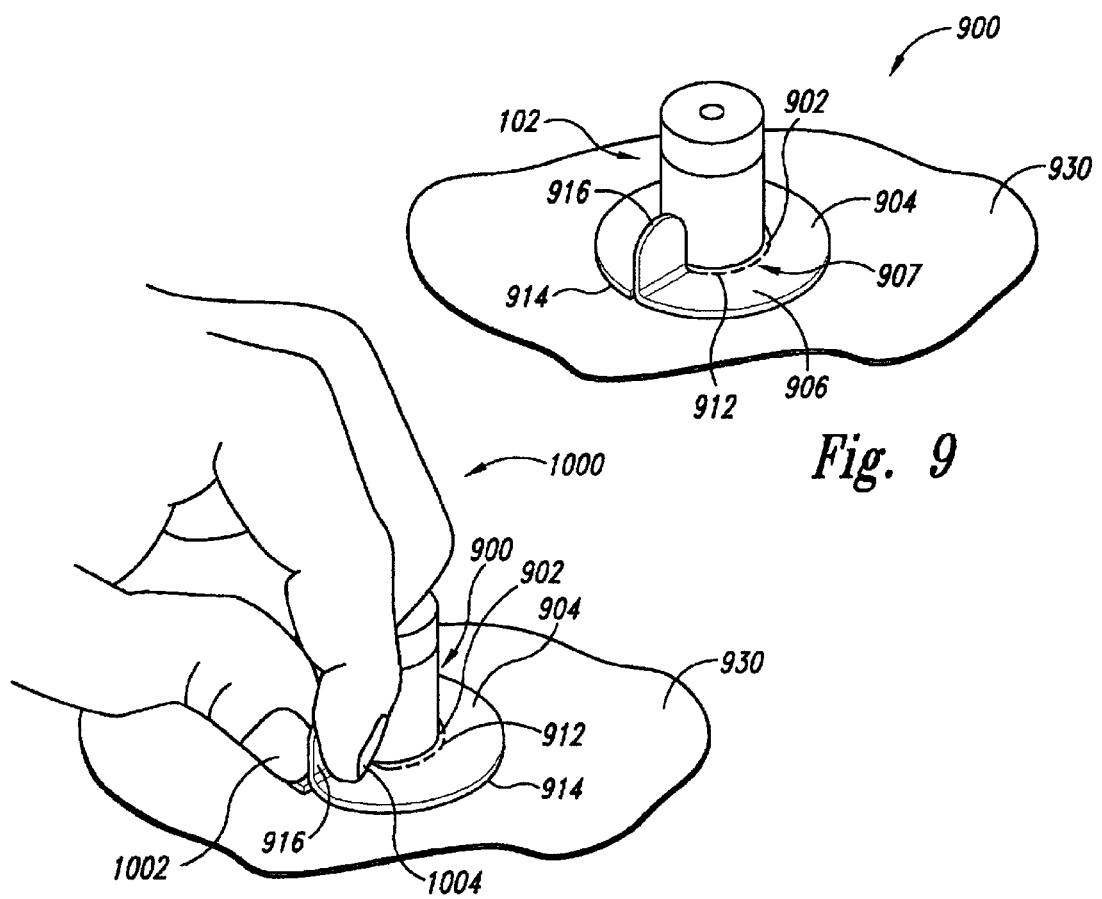
FIG. 9 is a top isometric view of an applicator having an attachment member in accordance with another embodiment of the invention.
Figure 10:
FIG. 10 is a top isometric view of the applicator shown in FIG. 9 grasped by a practitioner in accordance with an embodiment of the invention.
Figure 11:
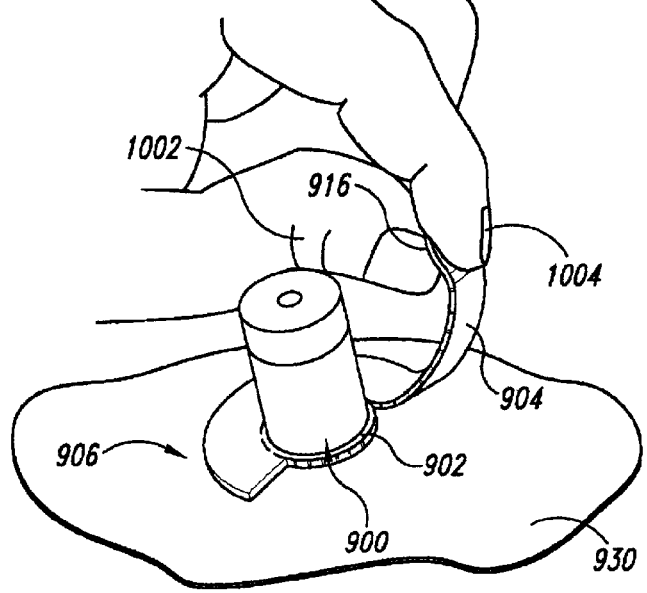
FIG. 11 is an isometric view of an applicator being detached from a skin surface in accordance with an embodiment of the invention.

FIGS. 9–11 schematically illustrate steps for removing an applicator 900 in accordance with an embodiment of the invention. Referring first to FIG. 9, the applicator 900 can include a housing 102 generally similar to that described above with reference to FIGS. 1–6. An attachment member 906 having an inner portion 902 attached to the housing 102 and an outer portion 904 attached to a patient's skin surface 930 releasably connects the applicator 900 to the patient. For example, the attachment member 906 can have an adhesive lower surface 914 engaged with the patient's skin surface 930. In one aspect of this embodiment, the second portion 904 can include an upwardly projecting tab 916 that can be conveniently grasped by the practitioner. Alternatively, the second portion 904 can include a tab that is generally coplanar with the patient's skin 930, as shown in FIGS. 1 and 3. In either embodiment, the attachment member 906 can include a releasable bond 907 that tends to separate along a tear line 912.

As shown in FIG. 10, a practitioner 1000 can grasp the tab 916 between a thumb 1002 and a forefinger 1004 and pull upwardly on the tab 916. The second portion 904 of the attachment member 906 will tend to separate from the first portion 902 along the tear line 912. As the second portion 904 separates from the first portion 902, it also breaks the adhesive bond between the adhesive lower surface 914 and the patient's skin 930, allowing the applicator 900 to be removed from the patient. FIG. 11 illustrates the applicator 900 after it has been released from the patient's skin 930, with the second portion 904 at least partially separated from the first portion 902.

One feature of the embodiments of the applicator described above with reference to FIGS. 1–11 is that the second portion of the attachment member can at least partially separate or tear away from the first portion as the applicator is removed from the patient's skin. One advantage of this feature is that the torn attachment member clearly indicates that the applicator has previously been attached to a patient, and can accordingly signal the practitioner not to re-use the applicator. Therefore, the practitioner may be less likely to spread pathogens transmitted by re-used percutaneous probes.

Another advantage of this arrangement is that the torn attachment member can make it difficult for the practitioner to reattach the applicator to the same or another recipient. For example, referring now to FIG. 11, it may be difficult to stably support the applicator 900 on the patient's skin with the attachment member 906 alone because a substantial part of the second portion 904 of the attachment member 906 is severed from the first portion 902. Accordingly, the severed part of the second portion 904 provides no support for the applicator 900, even if the severed part has enough remaining adhesive strength to reattach to the patient. Furthermore, the adhesive strength of the second portion 904 can be diminished after one use because (a) a portion of the adhesive remains on the patient's skin 300, and/or (b) the adhesive remaining on the second portion 904 may be less tacky because it has picked up material (such as dead skin cells) from the patient's skin.

Nevertheless, it may be possible for a practitioner to reattach the applicator 900 to the same or another recipient (after the applicator 900 has been detached) despite the clear indication presented by the applicator 900 that it has already been used, and despite the difficulty associated with reattaching the used applicator 900. For example, the practitioner can apply a separate adhesive (such as a film adhesive or a liquid adhesive) between the torn part of the second portion 704 and either the first portion 702 or the housing 102. The practitioner can then re-adhere the adhesive lower surface 914 of the second portion 904 to a skin surface. Accordingly, the practitioner can re-establish a stable connection between the applicator 900 and the same or another patient. In other embodiments, the practitioner may reattach the applicator 900 with other methods.

Figure 12:
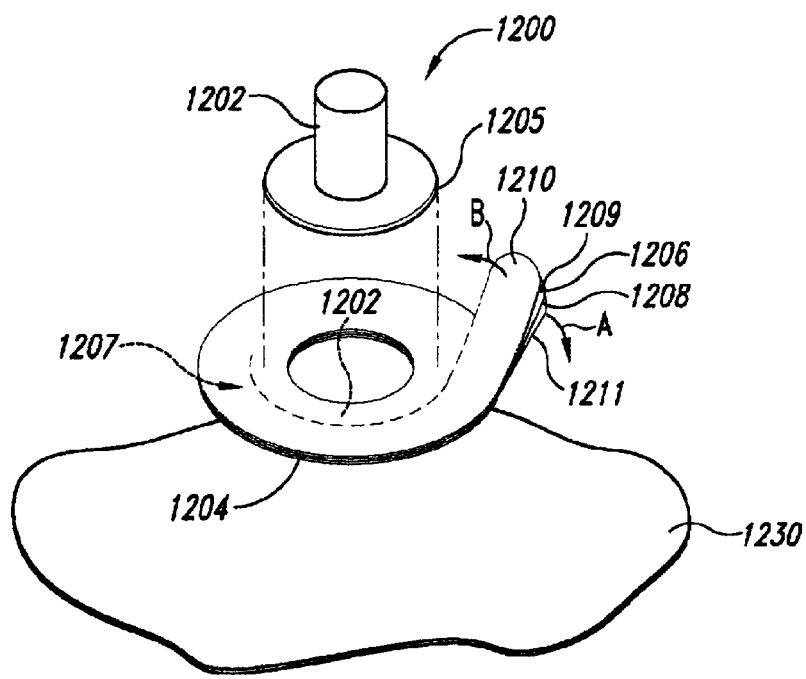
FIG. 12 is a partially schematic, partially exploded isometric view of an applicator assembly in accordance with another embodiment to the invention.

FIG. 12 is a partially schematic, isometric view of an applicator 1200 that is releasably attached to a recipient's skin surface 1230 in accordance with another embodiment to the invention. In one aspect of this embodiment, the applicator 1200 can include a housing 1202 having a flange 1205, and an attachment member 1206 that is initially separate from the housing 1202. The attachment member 1206 can have an adhesive lower surface 1208 and an adhesive upper surface 1209. A lower cover 1211 is initially positioned against the adhesive lower surface 1208, and an upper cover 1210 is initially positioned against the adhesive upper surface 1209. The attachment member 1206 can optionally include a first portion 1202 joined to a second portion 1204 with a releasable bond 1207, shown in phantom lines in FIG. 12.

In operation, a practitioner (not shown) removes the lower cover 1211 from the lower surface 1208 (as indicated by arrow A) and attaches the lower surface 1208 to the skin surface 1230. The practitioner can then remove the upper cover 1210 from the upper surface 1209 of the attachment member 1206 (as indicated by arrow B) and attach the flange 1205 of the applicator 1200 to the now exposed upper surface 1209. To release the applicator 1200 from the skin surface 1230, the practitioner can separate the lower surface 1208 of the attachment member 1206 from the skin surface 1230 while the attachment member 1206 remains attached to the flange 1205. Accordingly, the upper surface 1209 of the attachment member 1206 can have a stronger affinity for the flange 1205 than the lower surface 1208 has for the skin surface 1230. Alternatively, the practitioner can first remove the flange 1205 from the upper surface 1209 of the attachment member 1206, and then remove the attachment member 1206 from the skin surface 1230. Accordingly, the upper surface 1209 can have a lesser affinity for the flange 1205 than the lower surface 1208 has for the skin surface 1230.

In either of the foregoing embodiments, the attachment member 1206 can have a substantially reduced ability to reattach to the same or a different recipient. For example, when the attachment member 1206 includes a perforated releasable bond 1207, the second portion 1204 of the attachment member can be at least partially separated from the first portion 1202, in a manner generally similar to that described above with reference to FIGS. 7–11. Alternatively, the ability of the adhesive on the lower surface 1208 of the attachment member 1206 to reattach can be substantially reduced for any of the reasons described above with reference to FIGS. 7–11.

Figure 13:
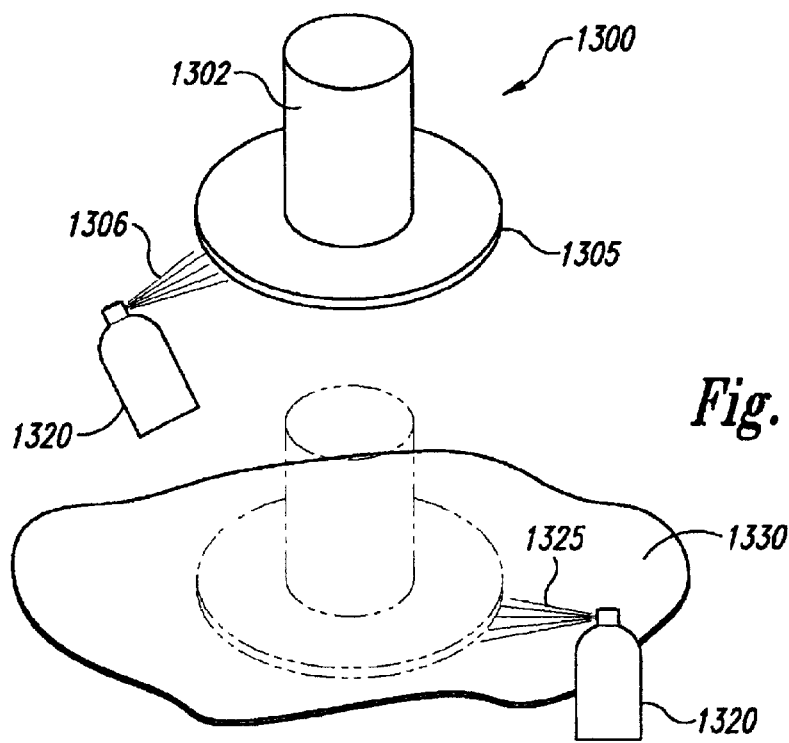
FIG. 13 is a partially schematic, isometric view of an applicator in accordance with yet another embodiment to the invention.

FIG. 13 is a partially schematic, isometric view of an applicator 1300 that is releasably connected to a recipient's skin surface 1330 in accordance with another embodiment of the invention. In one aspect of this embodiment, the applicator 1300 can include a housing 1302 having a flange 1305. The practitioner can apply a releasable adhesive 1306 to a lower surface of the flange 1305, for example, with an aerosol or pump-action spray applicator 1320. The practitioner can then engage the flange 1305 with the skin surface 1330. To remove the applicator 1300 from the skin surface 1330, the practitioner can dispose a release agent 1325 at or near the bond between the flange 1305 and the skin surface 1330. For example, the practitioner can deploy a spray of the release agent 1325 with a spray applicator 1330. In one embodiment, the adhesive 1306 can include a bonding agent such as cyanacrylate or cyanacrylic ester, and the release agent 1325 can include acetone. In other embodiments, the adhesive 1306 and the release agent 1325 can include other chemical compositions. In any of these embodiments, an advantage of chemically releasing the adhesive bond between the applicator 1300 and the skin surface 1330 is that the technique can apply less mechanical force to the recipient's skin 1330, which can be more comfortable for recipients who have sensitive skin.

Figure 14A:
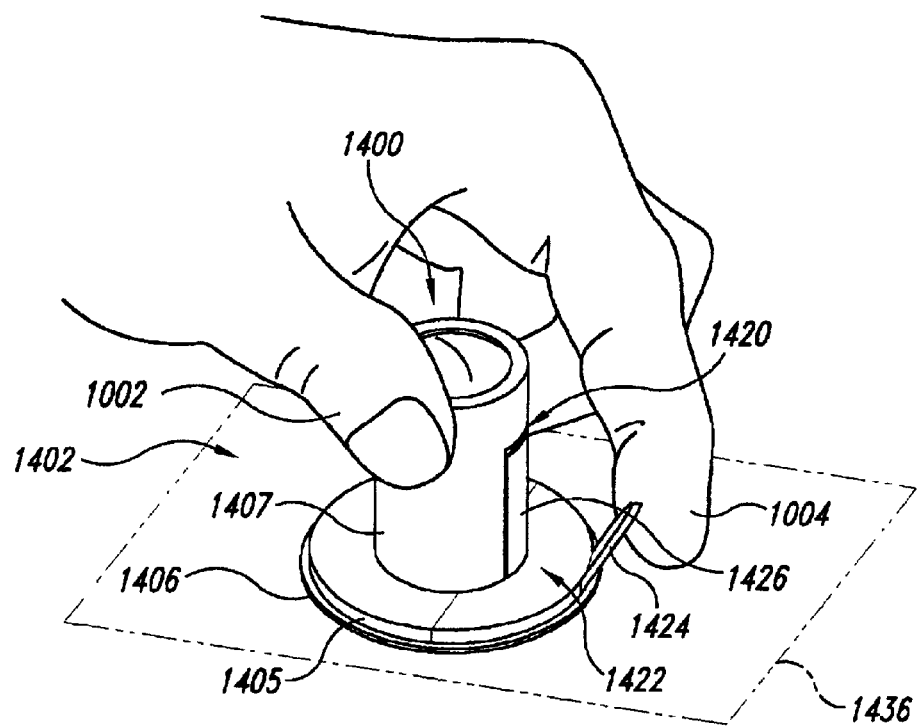
FIG. 14A is an isometric view of an applicator having a stop member in accordance with an embodiment of the invention.

FIG. 14A is an isometric view of an applicator 1400 having a stop member 1422 that at least restricts motion of a percutaneous probe following an initial use. In one aspect of this embodiment, the applicator 1400 can include a housing 1402 attached to the patient with an adhesive attachment member 1406 (positioned in a generally flat attachment plane 1436), generally in accordance with the embodiments discussed above. In one aspect of this embodiment, the housing 1402 can include a tube 1407 projecting upwardly from an annular lip 1405. The tube 1407 can have an aperture 1420 in which the stop member 1422 is positioned. The stop member 1422 can include a tab portion 1424 configured to be engaged by the practitioner's finger 1004, and an engaging portion 1426 configured to at least restrict motion of the percutaneous probe, as described in greater detail below with reference to FIGS. 14B–15B.

Figure 14B:
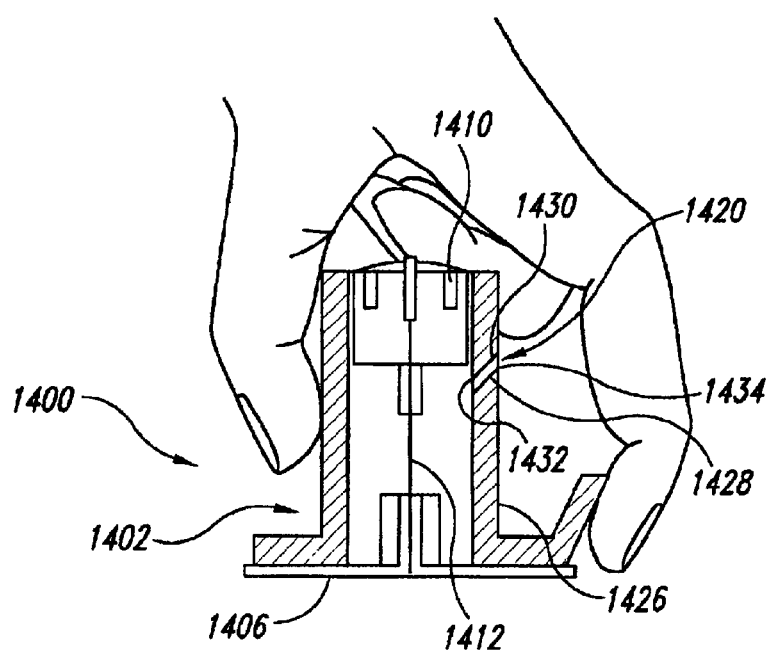
FIG. 14B is a cross-sectional side elevational view of the applicator shown in FIG. 14A.

FIG. 14B is a partially schematic, cross-sectional side elevational view of the applicator 1400 described above with reference to FIG. 14A. As shown in FIG. 14B, the applicator 1400 can include a slider 1410 having a percutaneous probe 1412. The slider 1410 is slidable (and, optionally, rotatable) relative to the housing 1402 to deploy and retract the percutaneous probe 1412 in a manner generally similar to that described above. In one aspect of this embodiment, a lower edge 1430 of the tube aperture 1420 can be downwardly inclined and parallel to an upper edge 1428 of the engaging portion 1426. In a further aspect of this embodiment, an innermost point 1432 of the lower edge 1430 can be positioned beneath an uppermost point 1424 of the upper edge 1428. Accordingly, the lower edge 1430 can lock the upper edge 1428 in a selected position, as described in greater detail below with reference to FIGS. 15A and 15B.

Figure 15A:
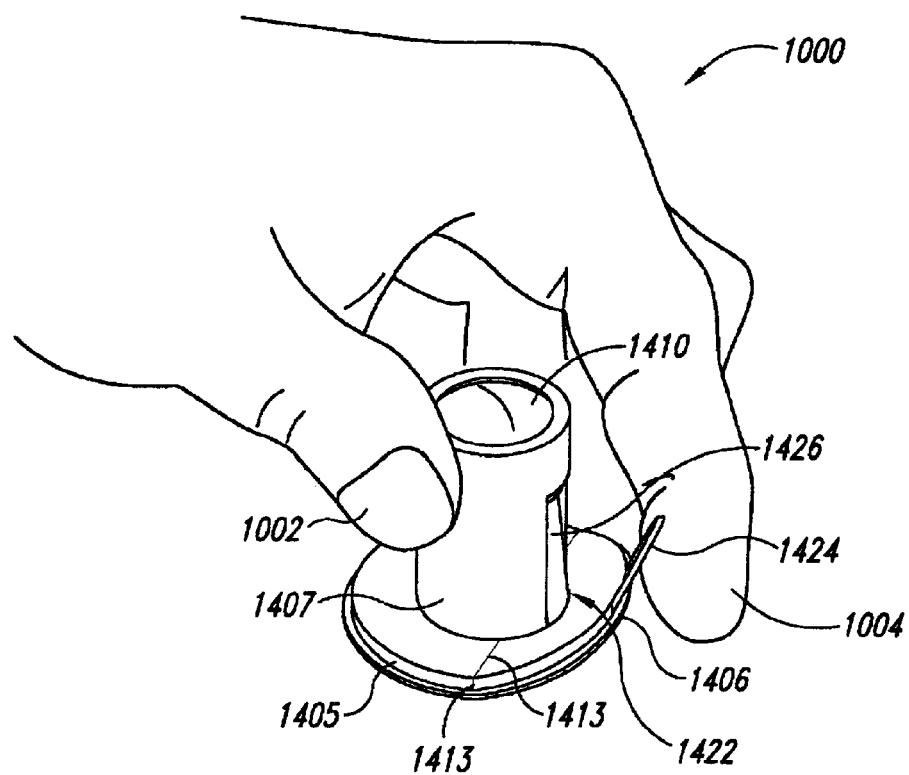
FIG. 15A is an isometric view of a practitioner moving the stop member of an applicator in accordance with an embodiment of the invention.
Figure 15B:
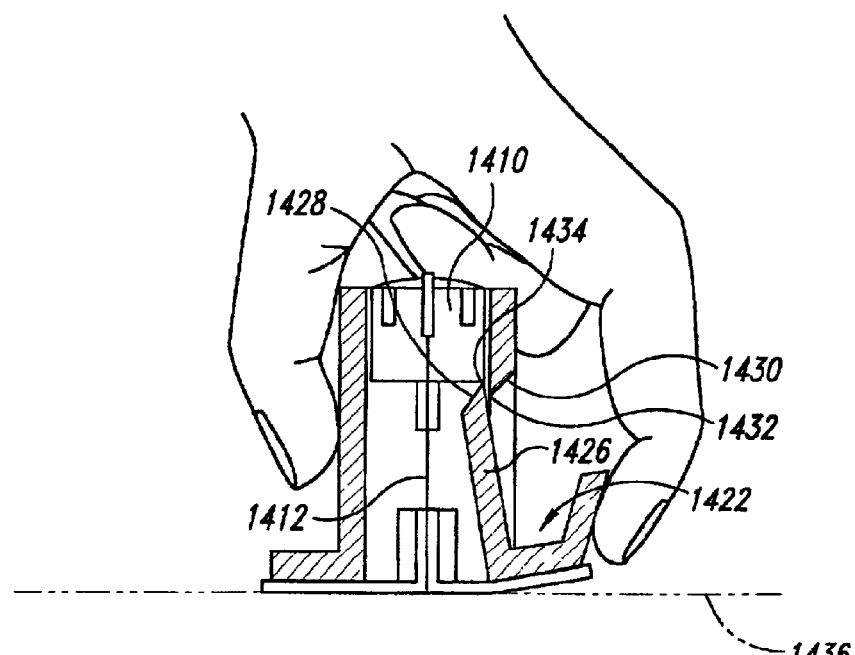
FIG. 15B is a cross-sectional side elevational view of the applicator shown in FIG. 15A.

Referring now to FIG. 15A, the practitioner 1000 can engage the tube 1407 with the thumb 1002 and engage the tab portion 1424 with the forefinger 1004. The practitioner can then rotate the tab portion 1424 toward the tube 1407 to fold a portion of the annular lip 1405 and the adhesive attachment member 1406 along a fold line 1413. As the stop member 1422 rotates inwardly, the engaging portion 1426 moves from a non-restricting position (coplanar with the walls of the tube 1407) to a restricting position (inward of the walls of the tube 1407 and just beneath the slider 1410). Referring now to FIG. 15B, the slider 1410 and probe 1412 are restricted by the stop member 1422 from moving downwardly to a deployed position. The stop member 1422 is at least impeded from moving to its non-restricting position because the uppermost point 1434 of the engaging portion 1426 is now "clicked" to a position inward from and above the innermost point 1432 of the aperture lower edge 1430.

One feature of an embodiment of the applicator 1400 described above with reference to FIGS. 14A–15B is that the stop member 1422 can prevent the slider 1410 and the probe 1412 from deploying when the stop member 1422 is in its restricting position. Another feature is that the stop member 1422 can move from the non-restricting position to the restricting position as the applicator 1400 is being removed from the skin surface. An advantage of these features is that the configuration of the applicator 1400 can alert a practitioner who attempts to remove the applicator before withdrawing the probe 1412. For example, if the slider 1410 is in its downward position with the probe 1412 deployed in the patient's skin, the slider 1410 will interfere with the inward motion of the engaging portion 1426, and the practitioner will be unable to "click" the engaging portion 1426 into the aperture 1420.

Another advantage of these features is that once the stop member 1422 is moved to its restricting position to prevent downward movement of the slider 1410 (as shown in FIG. 15B), the applicator 1400 cannot be easily re-used. Furthermore, the partially folded annular lip 1405 and the inwardly rotated stop member 1422 can provide a visual indicator to the practitioner that the applicator 1400 has been used and is not suitable for reuse. Accordingly, the stop member 1422 can reduce the likelihood for transmitting pathogens via re-used applicators and percutaneous probes 1412.

Still another advantage of the features described above is that the tab portion 1424 can pull up part of the attachment member 1406 as the practitioner pivots the tab portion 1424 into the tube 1407. Accordingly, the tab portion 1424 can initiate the separation of the attachment member 1406 from the patient's skin and make continued removal of the applicator 1400 easier.

Yet another advantage of the foregoing features is that the practitioner can be inhibited from re-attaching the applicator 1400 to another recipient after an initial use. For example, as the engaging portion 1426 of the stop member 1422 is moved to its restricting position, the tab portion 1424 can pull up part of the attachment member 1406 and deflect this part of the attachment member from the generally flat attachment plane 1436. The tab portion 1424 is restricted from moving this part of the attachment member 1406 back into the attachment plane 1436 because the engaging portion 1426 is restricted from rotating outwardly by the lower tip 1432 of the aperture 1420. The applicator 1400 will not attach as readily or as stably to the patient when part of the attachment member 1406 is deflected from the attachment plane 1436.

Nevertheless, it may be possible for a practitioner to re-use the applicator 1400 despite the clear indication presented by the applicator 1400 that it has already been used, and despite the position of the stop member 1422. For example, the practitioner can apply a downward force to the tab portion 1424 to force the uppermost point 1434 of the stop member 1422 outwardly past the innermost point 1432 of the aperture lower edge 1430. In other embodiments, the practitioner may circumvent the stop member 1422 in other manners.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

What is claimed is:

1. An apparatus for administering percutaneous electrical therapy to a recipient, comprising:
   a percutaneous electrode;
   a housing supporting the percutaneous electrode in position for penetrating a skin surface of the recipient; and
   a releasable attachment member having a first portion connected to the housing, the attachment member further having a second portion with an attachment surface facing away from the housing and adapted to engage the skin surface, a releasable bond coupling the second portion to the first portion wherein the releasable bond strength is less than a tear strength of the first portion and less than a tear strength of the second portion, and wherein the first and second portions of the attachment member are formed integrally with each other, and wherein the releasable bond includes perforations between the first and second portions.

2. The apparatus of claim 1 wherein the releasable bond includes a plurality of connecting portions arranged along a line between the first and second portions, the connecting portions being separated by interstitial spaces.

3. The apparatus of claim 1 wherein the releasable bond includes a plurality of connecting portions arranged along a line between the first and second portions, the connecting portions being separated by interstitial spaces, the connecting portions being formed integrally with the first and second portions of the attachment member.

4. The apparatus of claim 1 wherein the attachment member includes a plurality of layers, the first portion having a first plurality of layers, the second portion having a second plurality of layers, and the releasable bond having a third plurality of layers with the third plurality being less than the first plurality and less than the second plurality.

5. The apparatus of claim 1 wherein the first portion includes a first material, the second portion includes a second material and the releasable bond includes a third material different than the first and second materials.

6. The apparatus of claim 5 wherein the first and second materials are the same.

7. The apparatus of claim 1 wherein the housing includes a generally cylindrical portion in which the percutaneous electrode is positioned, the housing further including a flange extending radially outwardly from the generally cylindrical portion toward one end of the generally cylindrical portion, and wherein the first portion of the attachment member is adhesively bonded to the flange and the second portion of the attachment member is positioned radially outwardly from the first portion.

8. The apparatus of claim 1 wherein the first and second portions are formed integrally with each other and have a first thickness in a direction generally normal to the engaging surface, and wherein the releasable bond is formed integrally with the first and second portions and has a second thickness in a direction generally normal to the engaging surface, the second thickness being less than the first thickness.

9. The apparatus of claim 1 wherein the housing has a generally cylindrical portion and the releasable band defines a generally arcuate bond line concentric with the generally cylindrical portion.

10. The apparatus of claim 1 wherein the second portion of the attachment member includes a tab having a non-adhesive surface to remain detached from the skin surface when the attachment surface of the attachment member is engaged with the skin surface.

11. The apparatus of claim 1 wherein the second portion of the attachment member includes a tab having a non-adhesive surface to remain detached from the skin surface when the attachment surface of the attachment member is engaged with the skin surface, the non-adhesive surface being generally co-planar with an adhesive surface.

12. The apparatus of claim 1 wherein the attachment surface includes an adhesive to attach to the skin surface when the attachment surface is engaged with the skin surface.

13. The apparatus of claim 12, further comprising a cover sheet releasably attached to the adhesive.

14. The apparatus of claim 1 wherein the attachment member includes a compressible material on the first and second portions whereby the compressible material is utilized on the second portion of the attachment member when connected to the housing and the first portion.

15. The apparatus of claim 1, wherein the percutaneous electrode is movable relative to the housing between a first position with the percutaneous electrode located within the housing and a second position with the percutaneous electrode at least partially external to the housing for penetrating the skin surface, and wherein the apparatus still further comprises a stop member coupled to the housing and movable relative to the housing between a non-restricting position and restricting position, the stop member being operatively decoupled from the percutaneous electrode when in the non-restricting position to allow axial motion of the electrode, the stop member being positioned to at least restrict axial motion of the percutaneous electrode when the stop member is in the restricting position.

16. The apparatus of claim 1 wherein the housing has a generally cylindrical casing with an aperture extending through the casing, and wherein the housing has at least one guide channel, and wherein the apparatus further comprises:
   a slider member supporting the percutaneous electrode and having at least one guide portion received in the guide channel, the slider member being movable relative to the housing to move the percutaneous electrode between a first position with the percutaneous electrode located within the housing and a second position with the percutaneous electrode at least partially external to the housing for penetrating the skin surface; and
   a stop member connected to the attachment member and movable relative to the housing between a non-restricting position and a restricting position, the stop member being disengaged from the slider member when in the non-restricting position to allow axial motion of the electrode between the first and second positions, the stop member being axially aligned with the slider member when in the restricting position to at least restrict motion of the percutaneous electrode away from the second position, the stop member having a tab portion positioned and adapted to be engaged by a human digit for movement between the non-restricting and the restricting position, the stop member further including an engaging portion positioned in the aperture of the casing, the engaging portion being generally co-planar with the casing when the stop member is in the non-restricting position, the engaging portion being positioned inwardly of the casing and aligned with the slider member when the stop member is the restricting position.

17. An apparatus for administering percutaneous electrical therapy to a recipient, comprising:

a support housing having an engaging surface positioned and adapted to engage a skin surface of the recipient;

a percutaneous electrode movably supported relative to the support housing and movable relative to the support housing toward and away from the engaging surface between a first position with the electrode a first distance from the engaging surface and a second position with the electrode a second distance away from the engaging surface; and an adhesive member having a first portion connected to the support housing, the adhesive member further having a second portion with an adhesive surface facing away from the housing and adapted to engage the skin surface, a releasable bond coupling the second portion to the first portion and wherein releasable bond strength is less than the first portion strength and less than the second portion strength, with the adhesive member preferentially separating at the releasable bond when a first force is applied to the first portion and a second force at least partially opposing the first force is applied to the second portion.

18. The apparatus of claim 17, wherein the first and second portions of the adhesive member are formed integrally with each other and wherein the releasable bond includes perforations between the first and second portions.

19. The apparatus of claim 17 wherein the releasable bond includes a plurality of connecting portions arranged along a line between the first and second portions, the connecting portions being separated by interstitial spaces.

20. The apparatus of claim 17 wherein the releasable bond includes a plurality of connecting portions arranged along a line between the first and second portions, the connecting portions being separated by interstitial spaces, the connecting portions being formed integrally with the first and second portions of the adhesive member.

21. The apparatus of claim 17 wherein the support housing includes a generally cylindrical portion in which the percutaneous electrode is positioned, the housing further including a flange extending radially outwardly from the generally cylindrical portion toward one end of the generally cylindrical portion, the flange carrying the engaging surface, and wherein the first portion of the attachment member is adhesively bonded to the flange and the second portion of the adhesive member is positioned radially outwardly from the first portion.

22. The apparatus of claim 17 wherein the second portion of the adhesive member includes a tab having a non-adhesive surface to remain detached from the skin surface when the adhesive surface of the attachment member is attached to the skin surface.

23. The apparatus of claim 17, further comprising a stop member coupled to the housing and moveable relative to the housing between a non-restricting position and a restricting position, the stop member being operatively decoupled from the percutaneous electrode when in the non-restricting position to allow axial motion of the electrode between the first and second positions, the stop member being positioned to at least restrict motion of the percutaneous electrode away from the second position when the stop member is in the restricting position.

24. An apparatus for administering percutaneous electrical therapy to a recipient, comprising:

a support housing having an engaging surface positioned and adapted to engage a skin surface of the recipient;

a percutaneous electrode movably supported relative to the support housing and movable relative to the support housing along an axis towards and away from the engaging surface between a first position with the electrode a first distance from the engaging surface and a second position with the electrode a second distance away from the engaging surface, the electrode being movable transverse to the axis relative to the support housing only when the probe is in the second position; and an adhesive member having a first portion connected to the support housing, the adhesive member further having a second portion with an adhesive surface facing away from the housing and adapted to engage the skin surface, a releasable bond coupling the second portion to the first portion and wherein the releasable bond strength is less than the first portion strength and less than the second portion strength, with the adhesive member preferentially separating at the releasable bond when opposing forces are applied to the first and second portions.

25. The apparatus of claim 24 wherein the first and second portions of the adhesive member are formed integrally with each other and wherein the releasable bond includes perforations between the first and second portions.

26. The apparatus of claim 24 wherein the support housing includes a generally cylindrical portion in which the percutaneous electrode is positioned, the housing further including a flange extending radially outwardly from the generally cylindrical portion toward one end of the generally cylindrical portion, the flange carrying the engaging surface, and wherein the first portion of the attachment member is adhesively bonded to the flange and the second portion of the adhesive member is positioned radially outwardly from the first portion.

27. The apparatus of claim 24 wherein the second portion of the adhesive member includes a tab having a non-adhesive surface to remain detached from the skin surface when the adhesive surface of the adhesive member is attached to the skin surface.

28. The apparatus of claim 24, further comprising a stop member coupled to the housing and moveable relative to the housing between a non-restricting position and a restricting position, the stop member being operatively decoupled from the percutaneous electrode when in the non-restricting position to allow axial motion of the electrode between the first and second positions, the stop member being positioned to at least restrict motion of the percutaneous electrode away from the second position when the stop member is in the restricting position.

29. The apparatus of claim 24 wherein the housing has a base and a receiving cylinder, and wherein the apparatus further comprises:

a sleeve positioned in the receiving cylinder and rotatable about the axis; and a slider member supporting the percutaneous electrode in a position parallel to and offset from the axis, the slider member being slideable relative to the sleeve and the housing along the axis.

30. An apparatus for administering percutaneous electrical therapy to a recipient comprising:

a percutaneous electrode;

a housing supporting a percutaneous electrode in position for penetrating the skin surface of the recipient; and a removable attachment member initially separate from the housing, the attachment member having a first portion with an adhesive upper surface positioned to adhere to the housing, the attachment member further having a second portion with an adhesive lower surface facing away from the upper surface and adapted to engage the skin surface, a releasable bond coupling the second portion to the first portion, and wherein a tear strength of the releasable bond is less than a tear strength of the first portion and less than a tear strength of the second portion.

31. The apparatus of claim 30 wherein the upper surface has a first adhesive and the lower surface has a second adhesive, the first adhesive being configured to form a first bond with the housing, the second adhesive being configured to form a second bond with the skin surface, the second bond being weaker than the first bond.

32. The apparatus of claim 30, further comprising a first releasable cover removably attached to the upper surface and a second releasable cover removably attached to the second surface.

33. The apparatus of claim 30 wherein the first and second portions of the attachment member are formed integrally with each other and wherein the releasable bond includes perforations between the first and second portions.

34. The apparatus of claim 30 wherein the support housing includes a generally cylindrical portion in which the percutaneous electrode is positioned, the housing further including a flange extending radially outwardly from the generally cylindrical portion towards one end of the generally cylindrical portion, and wherein the first portion of the attachment member is shaped to adhesively bond to the flange and the second portion of the attachment member is positioned radially outwardly from the first portion.

35. The apparatus of claim 30 wherein the housing has a generally cylindrical portion and the releasable bond defines a generally arcuate bond line concentric with the generally cylindrical portion.

36. The apparatus of claim 30, further comprising the percutaneous electrode, and wherein the percutaneous electrode is movable relative to the housing between a first position with the percutaneous electrode located within the housing and a second position with the percutaneous electrode at least partially external to the housing to penetrate he skin surface, and wherein the apparatus still further comprises a stop member coupled to the housing and moveable relative to the housing between a non-restricting position and a restricting position, the stop member being operatively decoupled from the percutaneous electrode when in the non-restricting position to allow axial motion of the electrode, the stop member being positioned to at least restrict axial motion of the percutaneous electrode when the stop member is in the restricting position.

* * * * *